United States Patent
Nakamura et al.

(10) Patent No.: US 9,447,118 B2
(45) Date of Patent: Sep. 20, 2016

(54) PREPARATION METHOD OF OPTICALLY ACTIVE DIAMINE COMPOUND

(71) Applicant: Daiichi Sankyo Company, Limited, Chuo-ku, Tokyo (JP)

(72) Inventors: Yoshitaka Nakamura, Yokohama (JP); Makoto Michida, Kanagawa (JP); Takeshi Kaneda, Kanagawa (JP)

(73) Assignee: Daiichi Sankyo Company, Limited, Chuo-ku (JP)

( * ) Notice: Subject to any disclaimer, the term of this patent is extended or adjusted under 35 U.S.C. 154(b) by 0 days.

(21) Appl. No.: 14/805,123

(22) Filed: Jul. 21, 2015

(65) Prior Publication Data

US 2016/0016974 A1    Jan. 21, 2016

Related U.S. Application Data

(63) Continuation of application No. PCT/JP2014/059247, filed on Mar. 28, 2014.

(30) Foreign Application Priority Data

Mar. 29, 2013 (JP) ................. 2013-072895

(51) Int. Cl.

| C07D 513/04 | (2006.01) |
|---|---|
| A61K 31/444 | (2006.01) |
| C07C 271/24 | (2006.01) |
| C07C 303/28 | (2006.01) |
| C07C 303/34 | (2006.01) |
| C07C 307/08 | (2006.01) |
| C07B 53/00 | (2006.01) |
| C07C 309/66 | (2006.01) |
| C07C 309/73 | (2006.01) |
| C07D 285/14 | (2006.01) |
| C07C 303/40 | (2006.01) |

(52) U.S. Cl.
CPC ........... *C07D 513/04* (2013.01); *A61K 31/444* (2013.01); *C07B 53/00* (2013.01); *C07C 271/24* (2013.01); *C07C 303/28* (2013.01); *C07C 303/34* (2013.01); *C07C 303/40* (2013.01); *C07C 307/08* (2013.01); *C07C 309/66* (2013.01); *C07C 309/73* (2013.01); *C07D 285/14* (2013.01)

(58) Field of Classification Search
CPC ................................................... C07D 513/04
See application file for complete search history.

(56) References Cited

U.S. PATENT DOCUMENTS

| 7,015,321 B2 * | 3/2006 | Nicolaou | C07D 277/04 540/489 |
|---|---|---|---|
| 7,192,968 B2 * | 3/2007 | Yoshino | C07D 213/56 514/248 |
| 7,365,205 B2 | 4/2008 | Ohta | |
| 7,576,135 B2 | 8/2009 | Ohta | |

(Continued)

FOREIGN PATENT DOCUMENTS

| EP | 1 415 992 A1 | 5/2004 |
|---|---|---|
| JP | 2012-36181 A | 2/2012 |

(Continued)

OTHER PUBLICATIONS

Yang "Inhibition of serine proteases by a new class of cyclosulfamide-based carbamylating agents" Archives of Biochemistry and Biophysics 475 (2008) 115-120.*

(Continued)

*Primary Examiner* — David K O'Dell
(74) *Attorney, Agent, or Firm* — Christensen O'Connor Johnson Kindness PLLC

(57) ABSTRACT

The problem to be solved is to provide a method for efficiently producing compounds (1) and (1a) that are important intermediate compounds in the production of FXa inhibitors (X) and (X-a). The solutions thereto are a method for producing a compound represented by the formula (8d) using a stereoselective intramolecular cyclization reaction, and a method for producing a compound (1f) or a salt thereof, or a hydrate thereof, which is characterized by desulfonylation of the compound (8d). In each formula, $R^{4a}$ represents a C1-C6 alkyl group, a benzyl group, etc.

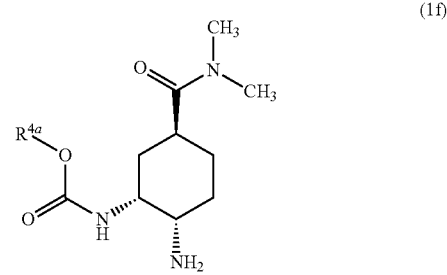

(1f)

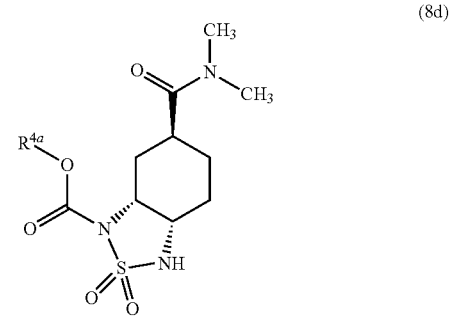

(8d)

27 Claims, No Drawings

(56) References Cited

U.S. PATENT DOCUMENTS

| | | |
|---|---|---|
| 7,935,824 B2 | 5/2011 | Yoshino |
| 8,686,189 B2 | 4/2014 | Sato |
| 2004/0138448 A1 | 7/2004 | Nicolaou |
| 2005/0245565 A1 | 11/2005 | Ohta |

FOREIGN PATENT DOCUMENTS

| | | |
|---|---|---|
| WO | 01/74774 A1 | 10/2001 |
| WO | 02/32858 A1 | 4/2002 |
| WO | 03/000657 A1 | 1/2003 |
| WO | 03/000680 A1 | 1/2003 |
| WO | 03/016302 A1 | 2/2003 |
| WO | 2004/058715 A1 | 7/2004 |
| WO | 2007/032498 A1 | 3/2007 |

OTHER PUBLICATIONS

Hannam "Rapid and Selective Synthesis of Substituted 1,2,5-Thiadiazolidine 1,1-Dioxides" SYNLETT 2006, No. 6, pp. 0833-0836.*

Valentekovich J. Am. Chem. Soc. 1995, 117, 9069-9070.*

Hua, Z., et al., "Summarization for the Synthesis and Application of Thiadiazoles Derivates," Journal of Bohai University (National Science Edition) 29(2)128-133, Jun. 2008.

Kurokawa, T., et al., "Synthesis of 1,3-Diamines Through Rhodium-Catalyzed C H Insertion," Angewandte Chemie International Edition 48(15)2777-2779, Mar. 2009.

Search Report mailed Mar. 15, 2016, issued in corresponding Chinese Application No. 2014800105618, filed Mar. 28, 2014, 2 pages.

Zhao, B., et al., "Cu(I)-Catalyzed Intermolecular Diamination of Activated Terminal Olefins," Organic Letters 9 (24):4943-4945, Dec. 2007.

International Search Report mailed Jul. 1, 2014, issued in corresponding International Application No. PCT/JP2014/059247, filed Mar. 28, 2014, 3 pages.

* cited by examiner

PREPARATION METHOD OF OPTICALLY ACTIVE DIAMINE COMPOUND

TECHNICAL FIELD

The present invention relates to a method for producing an intermediate of a compound that exhibits an inhibitory effect on activated blood coagulation factor X (FXa) and that is useful as a preventive and/or therapeutic drug for thrombotic diseases.

BACKGROUND ART

As compounds that exhibit an inhibitory effect on activated blood coagulation factor X [which is also referred to as an "FXa (activated Factor X)"], for example, $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide [hereinafter also referred to as "compound (X)"] represented by the following formula (X):

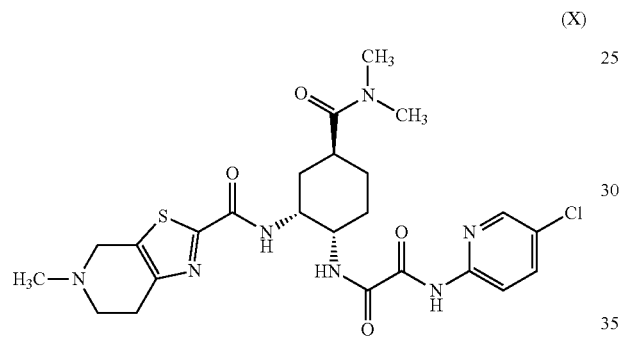

or a salt thereof, or a hydrate thereof, or a p-toluenesulfonic acid monohydrate of compound (X), which is represented by the following formula (X-a):

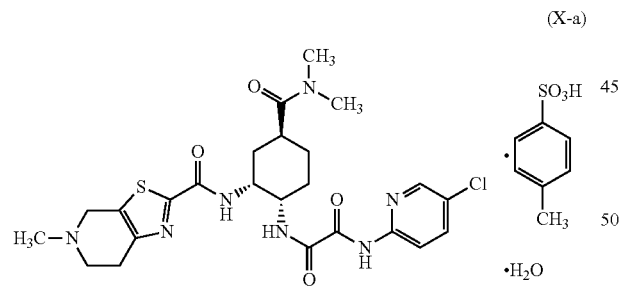

are known (see, for example, Patent Literatures 1 to 4).

For example, Patent Literature 6 discloses a method for producing compound (X) that is an FXa inhibitor or a pharmacologically acceptable salt thereof, or a hydrate thereof. As shown in the following [Scheme A], the method for producing compounds (X and X-a) disclosed in Patent Literature 6 comprises: producing compound (A-7) that is an azide form from compound (A-5) via compound (A-6) that is a mesyloxy form; then reducing the compound (A-7) to obtain compound (1a) that is an amino form; then treating the compound (1a) with oxalic acid to obtain compound (1); then treating the compound (1) with ethyl 2-[(5-chloropyridin-2-yl)amino]-2-oxoacetate monohydrochloride (A-8) in the presence of a base to produce compound (A-9), and further performing several steps after production of the compound (A-9). Patent Literature 6 discloses that compound (1a) and compound (1) that is an oxalate of the compound (1a) are important as production intermediates in the production of compound (X) that is an FXa inhibitor.

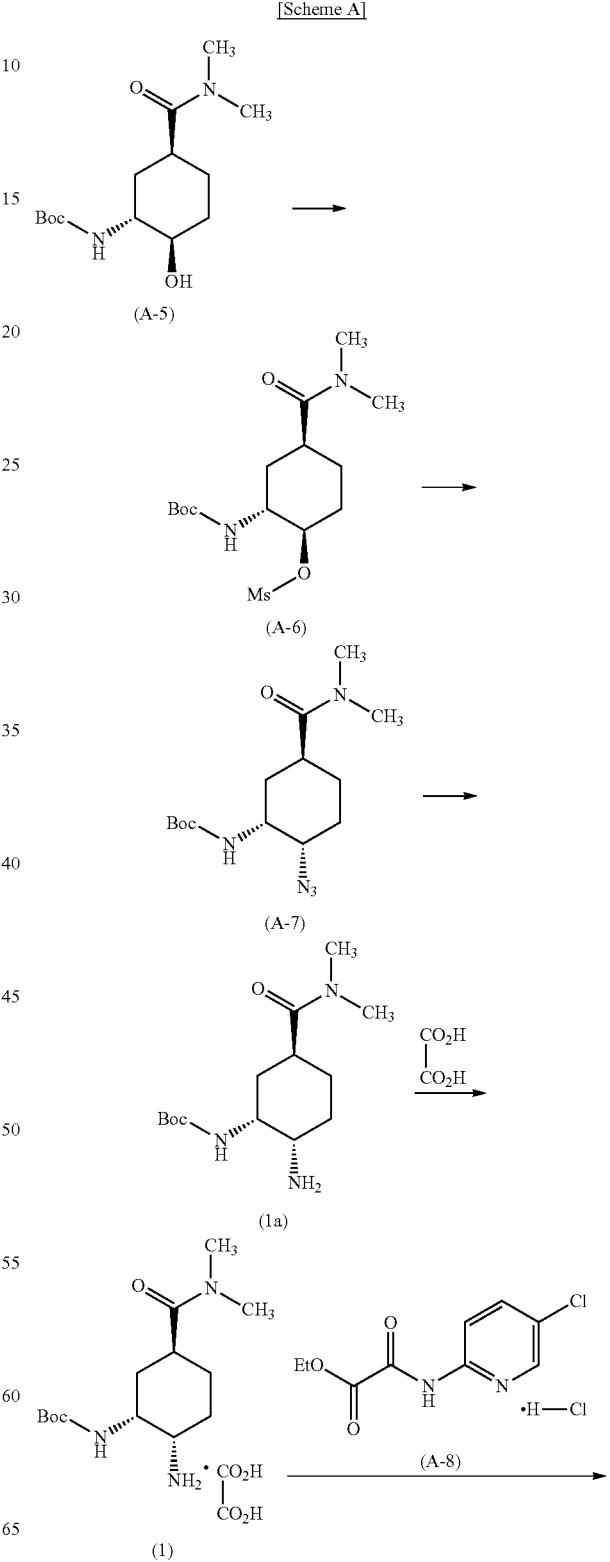

-continued

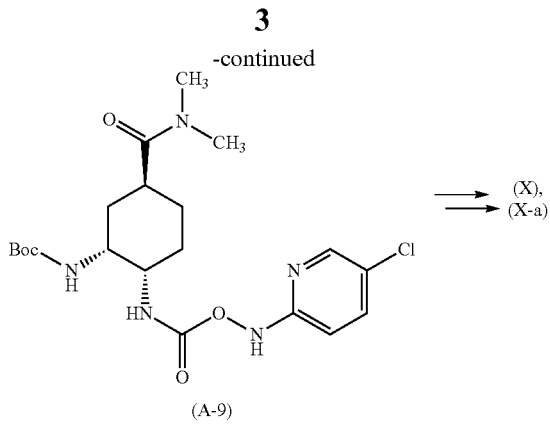

(A-9)

→ (X), (X-a)

wherein Boc represents a tert-butoxycarbonyl group; and Ms represents a methanesulfonyl group.

However, the method for producing compound (1 or 1a) disclosed in Patent Literature 6 has the following problems (a) and (b).

(a): The use of compound (A-7) having a potentially harmful azide group as an intermediate. Specifically, the use of compound (A-7) as an intermediate is problematic in that mass production of compound (A-7) that is an azide form requires the use of a large amount of an azide, which is a dangerous reagent, as a reaction reagent, in that mass production of compound (1) that is an amino form requires reduction of a large amount of compound (A-7) that is an azide form in the presence of a heavy metal catalyst such as Pd in pressure-resistant equipment and the like, and in that it is necessary to control mixing of the heavy metal into the product.

(b): In the azidation reaction (the nucleophilic substitution reaction of an azide group) in the production of compound (A-7) that is an azide form, in addition to the desired compound (A-7), a compound represented by the following formula (A-7-trans) that is a trans-isomer substituted in the trans-configuration with respect to the adjacent tert-butoxycarbonylamino group:

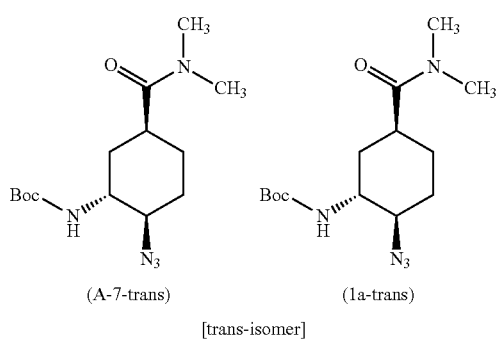 [SMILES: CN(C)C(=O)[C@H]1CC[C@@H](N=[N+]=[N-])[C@H](NC(=O)OC(C)(C)C)C1 ; CN(C)C(=O)[C@H]1CC[C@@H](N=[N+]=[N-])[C@H](NC(=O)OC(C)(C)C)C1]

[trans-isomer]

is generated as a stereoisomer at a percentage of approximately 10% to 15%. The subsequent reduction reaction progresses while the configuration is retained, and compound (A-7-trans) that is an azide form gives a compound (1a-trans) that is an amino form as a result of the reduction reaction. Accordingly, in order to obtain compound (1a) of interest in the cis-configuration at high purity, it is necessary to isolate and purify the desired compound (A-7) at the stage of the azide form, and therefore, a purification step using silica gel column chromatography or the like has been required (see, for example, Patent Literatures 1 to 5). On the other hand, in Patent Literature 6, a mixture of compound (1a) that is an amino form and the compound (1a-trans) that is a trans-isomer of the compound (1a) is treated with oxalic acid to obtain compound (1) that is an acid-added salt with the oxalic acid, so that the compound is substantially obtained in the form of a single cis-isomer.

However, as a method for producing compound (1) and compound (1a) that are important intermediates in the production of compounds (X) and (X-a) that are FXa inhibitors, only the aforementioned method via compound (A-7) that is an azide form, which causes many problems [(a) and (b)] as described above, is known so far (see, for example, Patent Literatures 1 to 6).

CITATION LIST

Patent Literatures

Patent Literature 1: International Publication No. WO 2003/000657
Patent Literature 2: International Publication No. WO 2003/000680
Patent Literature 3: International Publication No. WO 2003/016302
Patent Literature 4: International Publication No. WO 2004/058715
Patent Literature 5: International Publication No. WO 2001/074774
Patent Literature 6: International Publication No. WO 2007/032498

SUMMARY OF INVENTION

Technical Problem

It is an object of the present invention to provide a method for efficiently producing compound (1) or compound (1a) that is an important intermediate in the production of FXa inhibitors (X) and (X-a).

Solution to Problem

The present inventors have conducted diligent studies with the aim of achieving the aforementioned object. As a result, the present inventors have succeeded in achieving a novel method for producing compound (1a) and compound (1), which does not proceed via compound (A-7) that is an azide form used as an intermediate in the production of compound (1a) and compound (1). Specifically, the present inventors have made possible the direct introduction of a diamino skeleton in the cis-configuration, by constructing a stereoselective (3aR,7aS)-octahydro-2,1,3 benzothiadiazole ring, utilizing an intramolecular cyclization substitution reaction, and also by performing desulfonylation to remove a sulfonyl group from a sulfamoyl partial structure. Moreover, the present inventors have found that the intramolecular cyclization substitution reaction progresses regioselectively. That is to say, the inventors have found that it is possible to produce a regioselective amino-protected form, thereby completing the present invention relating to the production of compound (1a) and compound (1) stereoselectively, regioselectively, and at a high yield.

Advantageous Effects of Invention

The present invention can be used as a novel method for industrially producing FXa inhibitors (X) and (X-a).

DESCRIPTION OF EMBODIMENTS

The present invention provides the following [1] to [27].
[1] A method for producing a compound represented by the following formula (1d) or a salt thereof, or a hydrate thereof:

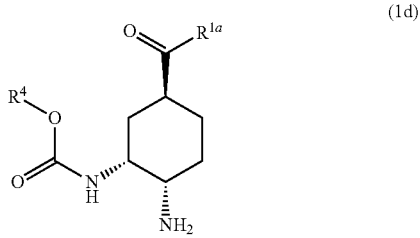

(1d)

wherein $R^{1a}$ represents a di(C1-C6 alkyl)amino group; and $R^4$ represents a C1-C6 alkyl group or a benzyl group (wherein the benzyl group may have, on the benzene ring, one or two groups as substituents selected from the group consisting of a C1-C6 alkyl group, a C1-C6 alkoxy group, a nitro group, and a halogen atom),
the method comprising:
treating a compound represented by the following formula (4):

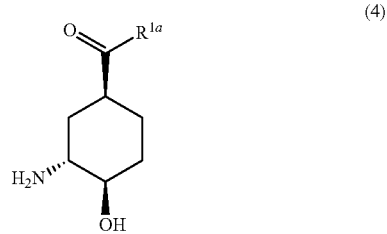

(4)

wherein $R^{1a}$ is as defined above,
with the following [solution A]:
[solution A] prepared by treating, in a solvent, a compound represented by the following formula (I):

$R^4$—OH (I)

wherein $R^4$ is as defined above, with chlorosulfonyl isocyanate and a tertiary amine; or
with the following [reagent B]:
[reagent B] that is a compound represented by the following formula (II):

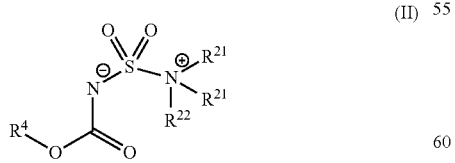

(II)

wherein $R^4$ represents a C1-C6 alkyl group or a benzyl group (wherein the benzyl group may have, on the benzene ring, one or two groups as substituents selected from the group consisting of a C1-C6 alkyl group, a C1-C6 alkoxy group, a nitro group, and a halogen atom); and $R^{21}$ and $R^{22}$ represent the following (a), (b) or (c):
(a) $R^{21}$ and $R^{22}$ are identical or different and each represent a C1-C6 alkyl group;
(b) $R^{22}$ represents a C1-C6 alkyl group, and the two $R^{21}$s, together with the nitrogen atom to which the $R^{21}$s binds, form a piperidine ring, a pyrrolidine ring or a 1,4-morpholine ring; or
(c) the two $R^{21}$s and $R^{22}$, together with the nitrogen atom to which $R^{22}$ and the $R^{21}$s bind, form a 1,4-diazabicyclo[2.2.2]octane ring or a quinuclidine ring, so as to obtain a compound represented by the following formula (5):

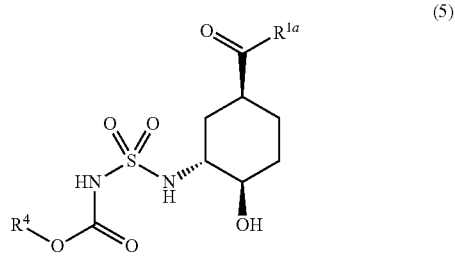

(5)

wherein $R^{1a}$ and $R^4$ are as defined above,
treating, in the presence of a base, the compound represented by the formula (5) with a compound represented by the following formula (III):

$R^6SO_2X$ (III)

wherein $R^6$ represents a C1-C6 alkyl group, a halo-C1-C6 alkyl group, or a phenyl group (wherein the phenyl group may have one or two groups as substituents selected from the group consisting of a C1-C6 alkyl group, a C1-C6 alkoxy group, a nitro group, and a halogen atom); and
X represents a halogen atom,
so as to obtain a compound represented by the following formula (6a):

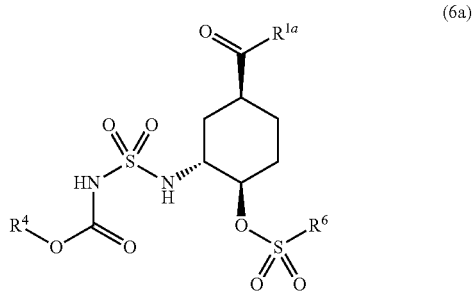

(6a)

wherein $R^{1a}$, $R^4$ and $R^6$ are as defined above,
treating the compound represented by the formula (6a) with a base to obtain a compound represented by the following formula (8c):

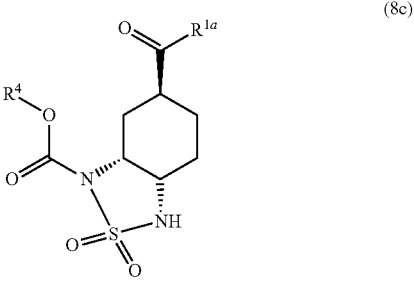

(8c)

wherein $R^{1a}$ and $R^4$ are as defined above, and
performing desulfonylation of the compound represented by the formula (8c).

[2] The production method according to [1], wherein the desulfonylation is carried out by treating the compound with water and a base.

[3] The production method according to [2], wherein the base is a pyridine.

[4] A method for producing a compound represented by the following formula (5):

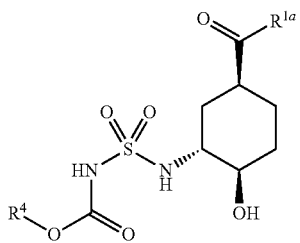

(5)

wherein $R^4$ represents a C1-C6 alkyl group or a benzyl group (wherein the benzyl group may have, on the benzene ring, one or two groups as substituents selected from the group consisting of a C1-C6 alkyl group, a C1-C6 alkoxy group, a nitro group, and a halogen atom); and
$R^{1a}$ represents a di(C1-C6 alkyl)amino group,
the method comprising treating a compound represented by the following formula (4):

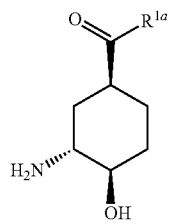

(4)

wherein $R^{1a}$ is as defined above, with the following [solution A]:

[solution A] prepared by treating, in a solvent, a compound represented by the following formula (I):

$R^4$—OH (I)

wherein $R^4$ is as defined above, with chlorosulfonyl isocyanate and a tertiary amine.

[5] A method for producing a compound represented by the following formula (5):

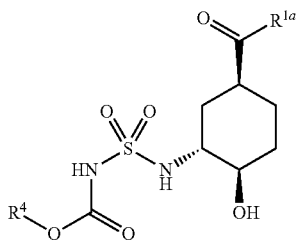

(5)

wherein $R^{1a}$ represents a di(C1-C6 alkyl)amino group; and
$R^4$ represents a C1-C6 alkyl group or a benzyl group (wherein the benzyl group may have, on the benzene ring, one or two groups as substituents selected from the group consisting of a C1-C6 alkyl group, a C1-C6 alkoxy group, a nitro group, and a halogen atom),
the method comprising treating a compound represented by the following formula (4):

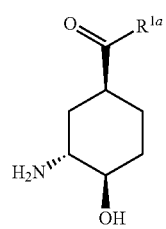

(4)

wherein $R^{1a}$ is as defined above, with the following [reagent B]:

[reagent B] that is a compound represented by the following formula (II):

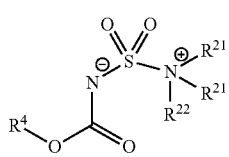

(II)

wherein $R^4$ is as defined above; and
$R^{21}$ and $R^{22}$ represent the following (a), (b) or (c):
(a) $R^{21}$ and $R^{22}$ are identical or different and each represent a C1-C6 alkyl group;
(b) $R^{22}$ represents a C1-C6 alkyl group, and the two $R^{21}$s, together with the nitrogen atom to which the $R^{21}$s bind, form a piperidine ring, a pyrrolidine ring or a 1,4-morpholine ring; or
(c) the two $R^{21}$s and $R^{22}$, together with the nitrogen atom to which $R^{22}$ and the $R^{21}$s bind, form a 1,4-diazabicyclo[2.2.2]octane ring or a quinuclidine ring.

[6] The production method according to [1] or [5], wherein $R^{21}$ and $R^{22}$ each represent an ethyl group.

[7] A method for producing a compound represented by the following formula (6a):

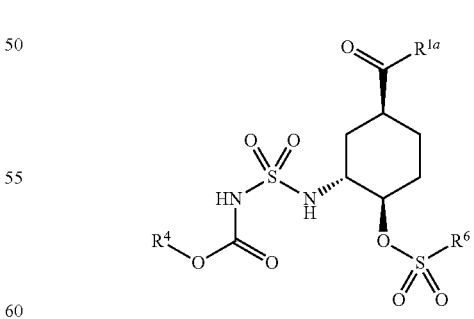

(6a)

wherein $R^{1a}$ represents a di(C1-C6 alkyl)amino group;
$R^4$ represents a C1-C6 alkyl group or a benzyl group (wherein the benzyl group may have, on the benzene ring, one or two groups as substituents selected from the group consisting of a C1-C6 alkyl group, a C1-C6 alkoxy group, a nitro group, and a halogen atom); and $R^6$ represents a C1-C6 alkyl group, a halo-C1-C6 alkyl group, or a phenyl group (wherein the phenyl group may have one or two groups as substituents selected from the group consisting of a C1-C6 alkyl group, a C1-C6 alkoxy group, a nitro group, and a halogen atom), the method comprising treating, in the presence of a base, a compound represented by the following formula (5):

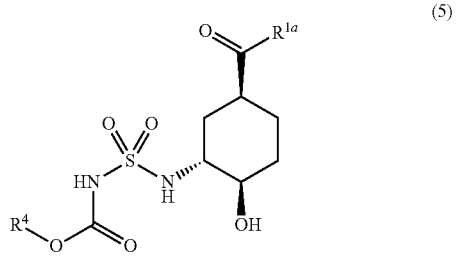
(5)

wherein $R^{1a}$ and $R^4$ are as defined above, with a compound represented by the following formula (III):

$R^6SO_2X$ (III)

wherein $R^6$ is as defined above; and
X represents a halogen atom.

[8] The production method according to [1] or [7], wherein $R^6$ represents a C1-C6 alkyl group.

[9] The production method according to [1] or [7], wherein $R^6$ represents a methyl group.

[10] A method for producing a compound represented by the following formula (8c):

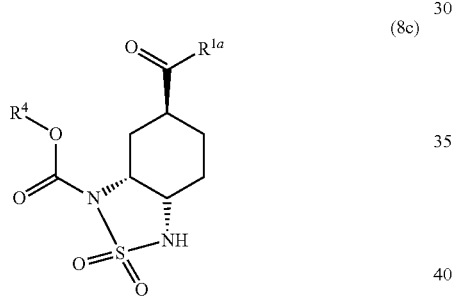
(8c)

wherein $R^{1a}$ represents a di(C1-C6 alkyl)amino group; and $R^4$ represents a C1-C6 alkyl group or a benzyl group (wherein the benzyl group may have, on the benzene ring, one or two groups as substituents selected from the group consisting of a C1-C6 alkyl group, a C1-C6 alkoxy group, a nitro group, and a halogen atom), the method comprising treating a compound represented by the following formula (6a):

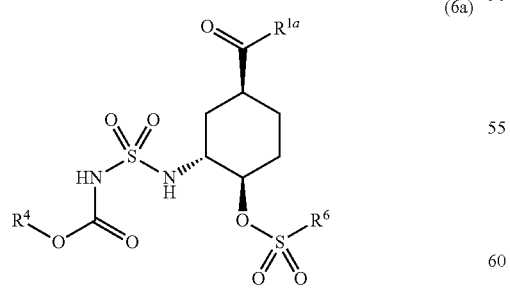
(6a)

wherein $R^{1a}$ and $R^4$ are as defined above; and
$R^6$ represents a C1-C6 alkyl group, a halo-C1-C6 alkyl group, or a phenyl group (wherein the phenyl group may have one or two groups as substituents selected from the group consisting of a C1-C6 alkyl group, a C1-C6 alkoxy group, a nitro group, and a halogen atom), with a base.

[11] A method for producing a compound represented by the following formula (1d) or a salt thereof, or a hydrate thereof:

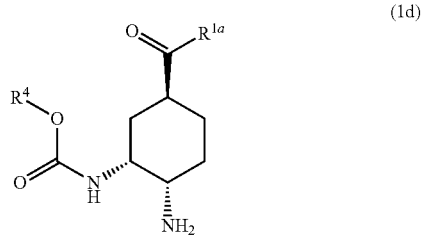
(1d)

wherein $R^{1a}$ represents a di(C1-C6 alkyl)amino group; and $R^4$ represents a C1-C6 alkyl group or a benzyl group (wherein the benzyl group may have, on the benzene ring, one or two groups as substituents selected from the group consisting of a C1-C6 alkyl group, a C1-C6 alkoxy group, a nitro group, and a halogen atom), the method comprising desulfonylation of a compound represented by the following formula (8c):

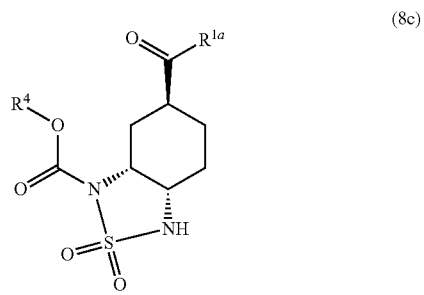
(8c)

wherein $R^{1a}$ and $R^4$ are as defined above.

[12] The production method according to [11], wherein the desulfonylation is carried out by treating the compound with water and a base.

[13] The production method according to [12], wherein the base is a pyridine.

[14] The production method according to any one of [1] to [13], wherein $R^{1a}$ is a di(methyl)amino group.

[15] The production method according to any one of [1] to [14], wherein $R^4$ is a tert-butyl group or a benzyl group.

[16] The production method according to [14] or [15], wherein the compound represented by the formula (1d) or a salt thereof, or a hydrate thereof is a sulfate of the compound represented by the formula (1d), an oxalate monohydrate of the compound represented by the formula (1d), or an oxalate of the compound represented by the formula (1d).

[17] A method for producing a compound represented by the following formula (1b) or a salt thereof, or a hydrate thereof:

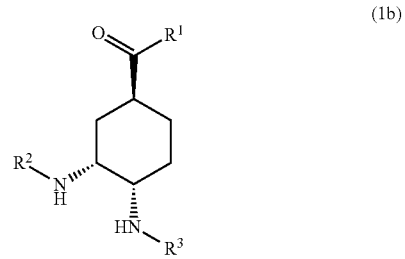
(1b)

wherein R² represents a C1-C6 alkoxy group or a di(C1-C6 alkyl)amino group; and

R² and R³ each independently represent a hydrogen atom, a C1-C6 alkoxycarbonyl group, or a benzyloxycarbonyl group (wherein the benzyl group may have, on the benzene ring, one or two groups as substituents selected from the group consisting of a C1-C6 alkyl group, a C1-C6 alkoxy group, a nitro group, and a halogen atom), the method comprising desulfonylation of a compound represented by the following formula (8a):

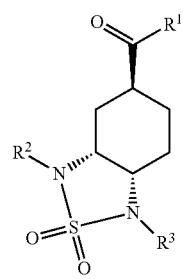

(8a)

wherein R¹, R² and R³ are as defined above.

[18] A method for producing a compound represented by the following formula (1c) or a salt thereof, or a hydrate thereof:

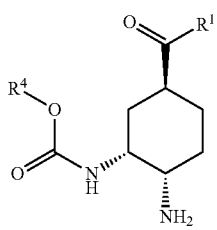

(1c)

wherein R¹ represents a C1-C6 alkoxy group or a di(C1-C6 alkyl)amino group; and

R⁴ represents a C1-C6 alkyl group or a benzyl group (wherein the benzyl group may have, on the benzene ring, one or two groups as substituents selected from the group consisting of a C1-C6 alkyl group, a C1-C6 alkoxy group, a nitro group, and a halogen atom), the method comprising desulfonylation of a compound represented by the following formula (8b):

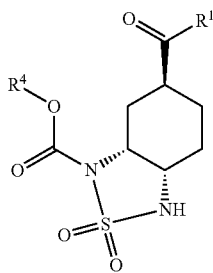

(8b)

wherein R¹ and R⁴ are as defined above.

[19] A compound represented by the following formula (5):

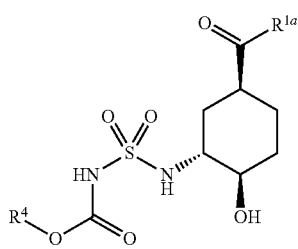

(5)

wherein R¹ᵃ represents a di(C1-C6 alkyl)amino group; and R⁴ represents a C1-C6 alkyl group or a benzyl group (wherein the benzyl group may have, on the benzene ring, one or two groups as substituents selected from the group consisting of a C1-C6 alkyl group, a C1-C6 alkoxy group, a nitro group, and a halogen atom).

[20] A compound represented by the following formula (6a):

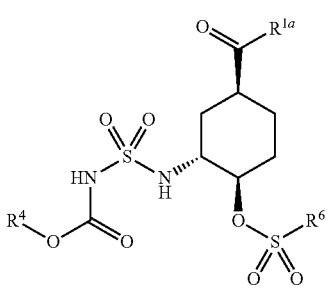

(6a)

wherein R¹ᵃ represents a di(C1-C6 alkyl)amino group;

R⁴ represents a C1-C6 alkyl group or a benzyl group (wherein the benzyl group may have, on the benzene ring, one or two groups as substituents selected from the group consisting of a C1-C6 alkyl group, a C1-C6 alkoxy group, a nitro group, and a halogen atom); and R⁶ represents a C1-C6 alkyl group, a halo-C1-C6 alkyl group, or a phenyl group (wherein the phenyl group may have one or two groups as substituents selected from the group consisting of a C1-C6 alkyl group, a C1-C6 alkoxy group, a nitro group, and a halogen atom).

[21] The compound according to [20], wherein R⁶ represents a C1-C6 alkyl group.

[22] The compound according to [20], wherein R⁶ represents a methyl group.

[23] A compound represented by the following formula (8c):

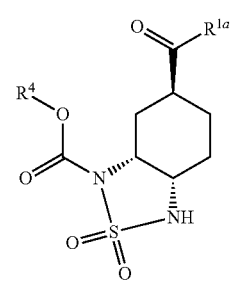

(8c)

wherein R¹ᵃ represents a di(C1-C6 alkyl)amino group; and $R^4$ represents a C1-C6 alkyl group or a benzyl group (wherein the benzyl group may have, on the benzene ring, one or two groups as substituents selected from the group consisting of a C1-C6 alkyl group, a C1-C6 alkoxy group, a nitro group, and a halogen atom).

[24] The compound according to any one of [19] to [23], wherein $R^{1a}$ represents a di(methyl)amino group.

[25] The compound according to any one of [19] to [23], wherein $R^4$ represents a tert-butyl group or a benzyl group.

[26] A method for producing a compound represented by the following formula (X-a):

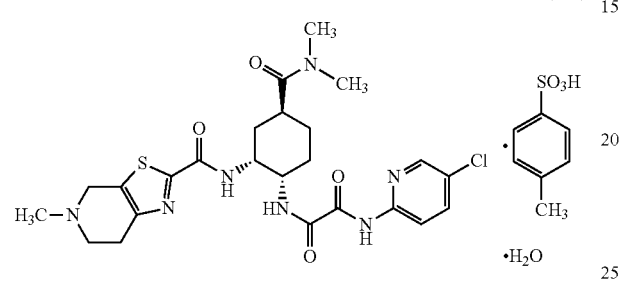
(X-a)

the method comprising: a step of
treating a compound represented by the following formula (8d):

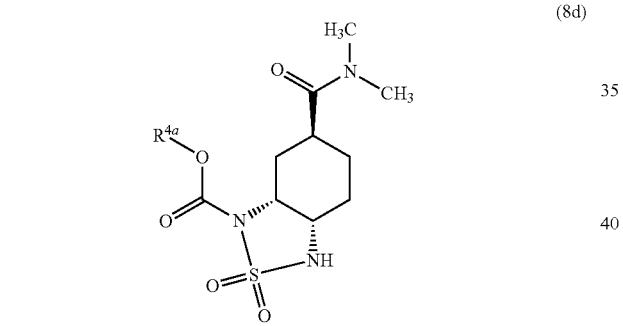
(8d)

wherein $R^{4a}$ represents a C1-C6 alkyl group or a benzyl group (wherein the benzyl group may have, on the benzene ring, one or two groups as substituents selected from the group consisting of a C1-C6 alkyl group, a C1-C6 alkoxy group, a nitro group, and a halogen atom), with water and a base, to obtain a compound represented by the following formula (1f):

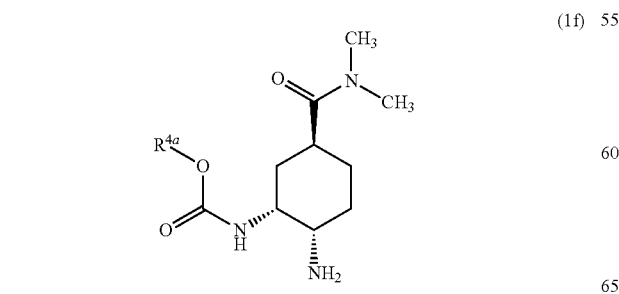
(1f)

wherein $R^{4a}$ is as defined above, treating, in the presence of a base, an oxalate or sulfate of the compound represented by the formula (1f) with a compound represented by the following formula (A-8):

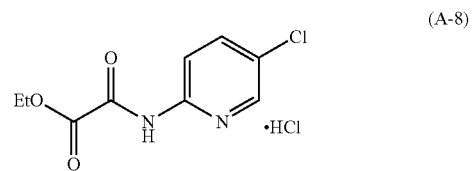 [SMILES: CCOC(=O)C(=O)Nc1ccc(Cl)cn1 ; Cl]
(A-8)

to obtain a compound represented by the following formula (A-9):

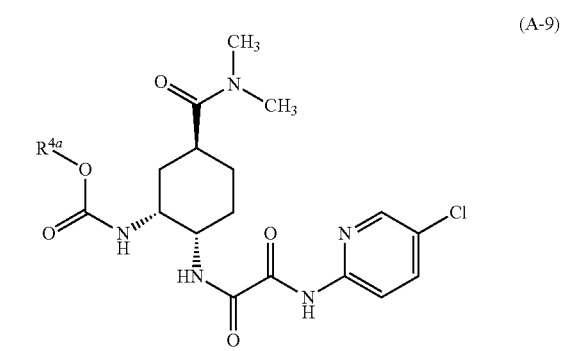
(A-9)

wherein $R^{4a}$ is as defined above, deprotecting the compound represented by the formula (A-9) to obtain a compound represented by the following formula (A-10):

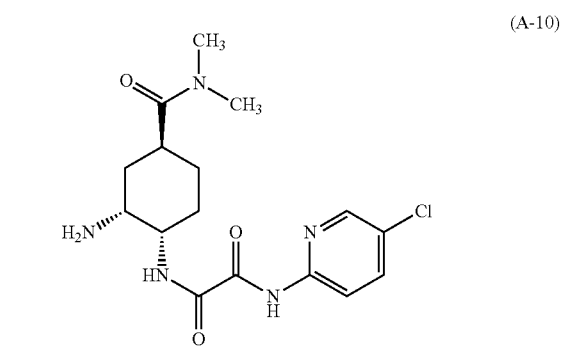 [SMILES: CN(C)C(=O)[C@H]1CC[C@H](NC(=O)C(=O)Nc2ccc(Cl)cn2)[C@H](N)C1]
(A-10)

and condensing the compound represented by the formula (A-10) or a salt thereof with a compound represented by the following formula (A-11):

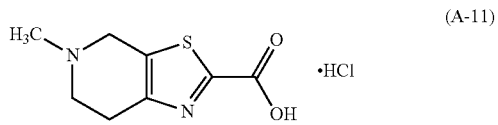
(A-11)

to obtain a compound represented by the following formula (X):

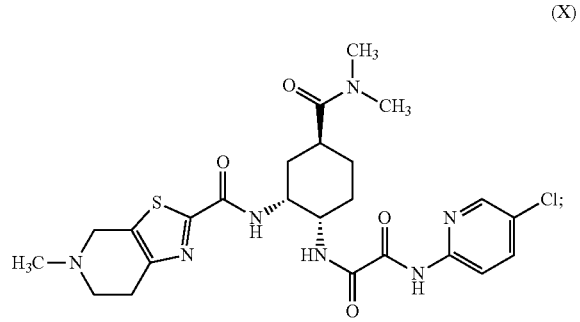 [SMILES: CN1CCc2nc(C(=O)N[C@@H]3C[C@@H](C(=O)N(C)C)CC[C@@H]3NC(=O)C(=O)Nc3ccc(Cl)cn3)sc2C1]

and a step of treating the compound represented by the formula (X) with p-toluenesulfonic acid monohydrate in aqueous ethanol.

[27] The production method according to [26], wherein $R^{4a}$ represents a tert-butyl group.

Hereinafter, the present invention will be described in detail.

A "halogen atom" in the present specification means a fluorine atom, a chlorine atom, a bromine atom, or an iodine atom.

A "C1 to C6 alkyl group" in the present specification means a linear or branched monovalent group having 1 to 6 carbon atoms, which is a saturated hydrocarbon. Examples of the C1 to C6 alkyl group can include methyl, ethyl, n-propyl, isopropyl, n-butyl, tert-butyl, n-pentyl, and n-hexyl.

A "halo-C1 to C6 alkyl group" in the present specification means the above described C1 to C6 alkyl group, which is substituted with 1 to 5 identical or different halogen atoms. Examples of the halo-C1 to C6 alkyl group can include fluoromethyl, difluoromethyl, trifluoromethyl, chloromethyl, dichloromethyl, trichloromethyl, fluoroethyl (which means both 1-fluoroethyl and 2-fluoroethyl), 2,2-difluoroethyl, 2,2,2-trifluoroethyl, 2,2,3,3,3-pentafluoroethyl, and fluoropropyl (which includes all of 3-fluoropropyl, 2-fluoropropyl, and 1-fluoropropyl).

A "C1-C6 alkoxy group" in the present specification means a C1 to C6 alkyloxy group formed of a C1 to C6 alkyl group and an oxygen atom. The C1-C6 alkyl is as described above. Examples of the C1-C6 alkoxy can include methoxy, ethoxy, n-propoxy, isopropoxy, n-butoxy, tert-butoxy, n-pentyloxy, and n-hexyloxy.

A "di(C1-C6 alkyl)amino group" in the present specification means an amino group substituted with two identical C1-C6 alkyl groups, and the C1-C6 alkyl group is as described above. Examples of the di(C1-C6 alkyl)amino can include di(methyl)amino, di(ethyl)amino, and di(n-propyl) amino.

Examples of a "C1-C6 alkoxycarbonyl group" in the present specification can include methoxycarbonyl, ethoxycarbonyl, n-propoxycarbonyl, isopropoxycarbonyl, n-butoxycarbonyl, and tert-butoxycarbonyl.

A "phenyl group" in the present specification means a monovalent group which may have a substituent(s) on the benzene ring, and it means that the phenyl group may have, on the benzene ring, one or two identical or different groups as substituents selected from the group consisting of a C1-C6 alkyl group, a C1-C6 alkoxy group, a nitro group, and a halogen atom. Examples of the phenyl group in the present specification include phenyl, p- (or o-)methylphenyl, p- (or o-)methoxyphenyl, 3,4-dimethoxyphenyl, p- (or o-)nitrophenyl, chlorophenyl, and 2,4-dichlorophenyl.

A "benzyl group" in the present specification means a monovalent group formed of a methyl group substituted with an optionally substituted phenyl group. It means that the phenyl group may have, on the benzene ring, one or two identical or different groups as substituents selected from the group consisting of a C1-C6 alkyl group, a C1-C6 alkoxy group, a nitro group, and a halogen atom. Examples of the benzyl group in the present specification include benzyl, p- (or o-)methylbenzyl, p- (or o-)methoxybenzyl, 3,4-dimethoxybenzyl, p- (or o-)nitrobenzyl, chlorobenzyl, and 2,4-dichlorobenzyl.

A "benzyloxycarbonyl group" in the present specification means a monovalent group formed of a methoxy group and a carbonyl group substituted with an optionally substituted phenyl group. It means that the phenyl group may have, on the benzene ring, one or two identical or different groups as substituents selected from the group consisting of a C1-C6 alkyl group, a C1-C6 alkoxy group, a nitro group, and a halogen atom. The benzyloxycarbonyl group used in the present specification is not particularly limited, as long as it is commonly used as a protecting group for amino groups. Herein, with regard to conditions for selection, introduction and removal of the "protecting group," and the like, publications described in review papers such as Protective Groups in Organic Synthesis (T. W. Green and P. G. M. Wuts, John Wiley & Sons, Inc., New York, 1991) may be referred. Examples of the benzyloxycarbonyl group include benzyloxycarbonyl, p- (or o-)methylbenzyloxycarbonyl, p- (or o-)methoxybenzyloxycarbonyl, 3,4-dimethoxybenzyloxycarbonyl, p- (or o-)nitrobenzyloxycarbonyl, chlorobenzyloxycarbonyl, and 2,4-dichlorobenzyloxycarbonyl.

A "C1-C6 alkylsulfonyloxy group" in the present specification means a monovalent group formed of a C1-C6 alkyl group and a sulfonyloxy group, and the C1-C6 alkyl group is as described above. Examples of the C1-C6 alkylsulfonyloxy group include methanesulfonyloxy, ethanesulfonyloxy, and n-propylsulfonyloxy.

A "halo-C1-C6 alkylsulfonyloxy group" in the present specification means a monovalent group formed of a halo-C1-C6 alkyl group and a sulfonyloxy group, and the halo-C1-C6 alkyl group is as described above. Examples of the halo-C1-C6 alkylsulfonyloxy group in the present specification include chloromethanesulfonyloxy, trifluoromethanesulfonyloxy, and (2,2,2-trifluoroethane)sulfonyloxy.

A "phenylsulfonyloxy group" in the present specification means a monovalent group formed of an optionally substituted phenyl group and a sulfonyloxy group. The phenyl group may have, on the benzene ring, one or two identical or different groups as substituents selected from the group consisting of a C1-C6 alkyl group, a C1-C6 alkoxy group, a nitro group, and a halogen atom. Examples of the phenylsulfonyloxy group include benzenesulfonyloxy, o-(m- or p-)chlorobenzenesulfonyloxy, 3,5-dichlorobenzenesulfonyloxy, o-(m- or p-)nitrobenzenesulfonyloxy, o-(m- or p-)methylbenzenesulfonyloxy(o-(m- or p-)toluenesulfonyloxy), and o-(m- or p-)methoxybenzenesulfonyloxy).

In the present invention, $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl] amino}cyclohexyl)ethanediamide represented by the following formula (X):

(X)

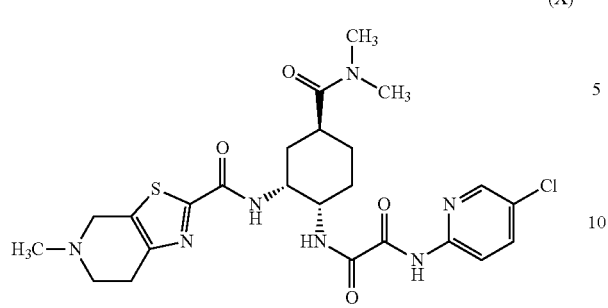

is the free form of compound (X-a), and this compound has been registered with the World Health Organization (WHO) as N-(5-chloropyridin-2-yl)-N'-[(1S,2R,4S)-4-(N,N-dimethylcarbamoyl)-2-(5-methyl-4,5,6,7-tetrahydro[1,3]thiazolo[5,4-c]pyridine-2-carboxamido)cyclohexyl]oxamide (International Nonproprietary Name (INN): edoxaban).

The above described compound (X) may be a pharmacologically acceptable salt thereof, or may also be a hydrate thereof. As such compound (X), the compound represented by the following formula (X-a):

(X-a)

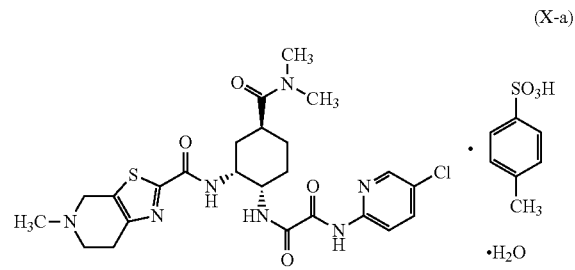 [SMILES: CN1CCc2nc(C(=O)N[C@@H]3C[C@@H](C(=O)N(C)C)CC[C@@H]3NC(=O)C(=O)Nc3ccc(Cl)cn3)sc2C1 ; O ; Cc1ccc(S(=O)(=O)O)cc1]

that is N¹-(5-chloropyridin-2-yl)-N²-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide p-toluenesulfonate monohydrate is preferable.

Hereinafter, the production method of the present invention will be described in detail.

As shown in [Scheme 1] below, one embodiment of the production method of the present invention relates to a method for producing a compound represented by formula (1b) as shown below that has a cis-diamino skeleton by constructing an octahydro-2,1,3-benzothiadiazole skeleton represented by formula (8a) as shown below that is a bicyclic compound in the cis-configuration, and by performing a deprotection reaction (desulfonylation) to remove a sulfonyl group from a sulfamoyl partial structure. Since the desulfonylation that is a deprotection reaction progresses in a stepwise manner, it is also possible to isolate the compound represented by formula (9) as shown below in the form of a salt, as desired.

[Scheme 1]

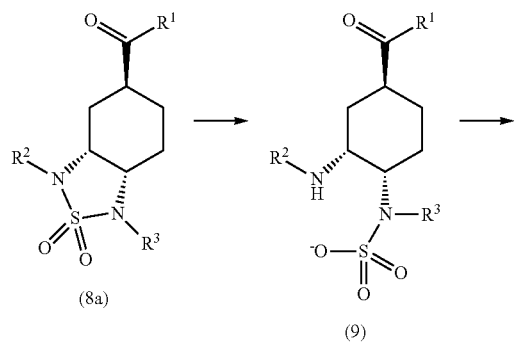

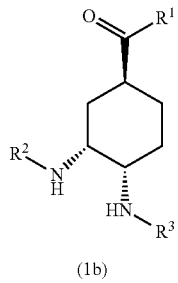

(1b)

wherein R² represents a C1-C6 alkoxy group or a di(C1-C6 alkyl)amino group;

R² and R³ each independently represent a hydrogen atom, a C1-C6 alkoxycarbonyl group, or a benzyloxycarbonyl group (wherein the benzyl group may have, on the benzene ring, one or two groups as substituents selected from the group consisting of a C1-C6 alkyl group, a C1-C6 alkoxy group, a nitro group, and a halogen atom).

As the above described reaction step, namely, as a deprotection reaction (desulfonylation reaction) to remove a "sulfonyl group (—S(O)₂—)" that is a protecting group for two amino groups, the reaction can be carried out by treating the compound with an acid or a base, so that two nitrogen-sulfur bonds in the thiadiazolidine ring are cleaved, according to known methods (see, for example, publications such as Organic Letters, 9(24), 4943-4945 (2007), Synlett, No. 6, 623-624 (1998), Angew. Chem. Int. Ed., Vol. 48(15), 2777-2779 (2009), or the pamphlet of Japanese Patent Laid-Open No. 2012-036181). The desulfonylation that is a deprotection reaction applied in the present invention is preferably a method of heating compound (8a) in a mixed solvent of water and a base. Herein, the sulfamic acid derivative (9), in which only one S—N bond is cleaved, is generated as an intermediate for the production of compound (1b) from compound (8a), and as described above, it can be isolated as desired. However, compound (8a) can be directly converted to compound (1b) by treating compound (8a) under heating in water and a base, without isolating compound (9) as an intermediate.

As a base used in the present deprotection reaction (desulfonylation reaction), either an organic base or an inorganic base can be used. Of these, an organic base is preferable; and preferred examples thereof include: ethylenediamines such as ethylenediamine and N,N,N',N'-(tetra-C1-C6 alkyl)ethylenediamine; pyridines such as pyridine, picoline (wherein the picoline includes all isomers such as α-picoline, β-picoline and γ-picoline), lutidine (wherein the lutidine includes all isomers such as 2,3-lutidine, 2,4-lutidine, 2,5-lutidine, 2,6-lutidine, 3,4-lutidine and 3,5-lutidine), collidine (wherein the collidine includes all isomers such as 2,3,4-collidine, 2,3,5-collidine, 2,3,6-collidine, 2,4,5-collidine, 2,4,6-collidine and 3,4,5-collidine), and 4-dimethylaminopyridine; and among these, pyridines such as pyridine are more preferable.

With regard to the additive ratio of water and base, the water and the base can be added at a ratio of 1:1 to 1:10 (V/V).

With regard to the reaction temperature, the reaction can be carried out in the range of 50° C. to the boiling point of a solvent, and preferably in the range of 70° C. to 85° C.

In the present step, an organic solvent may be used as a reaction auxiliary solvent. The organic solvent is not particularly limited, as long as it does not inhibit the reaction. Examples thereof include ether solvents such as tetrahydrofuran or dioxane, halogenated hydrocarbon solvents, aromatic hydrocarbon solvents, nitrogen-containing solvents such as acetonitrile, N,N-dimethylformamide, N,N-dimethylacetamide or N-methyl pyrrolidone, ketone solvents, and mixed solvents thereof.

In addition, the present invention provides a method for producing compound (1c) from compound (8b), as shown in the following [Scheme 2].

[Scheme 2]

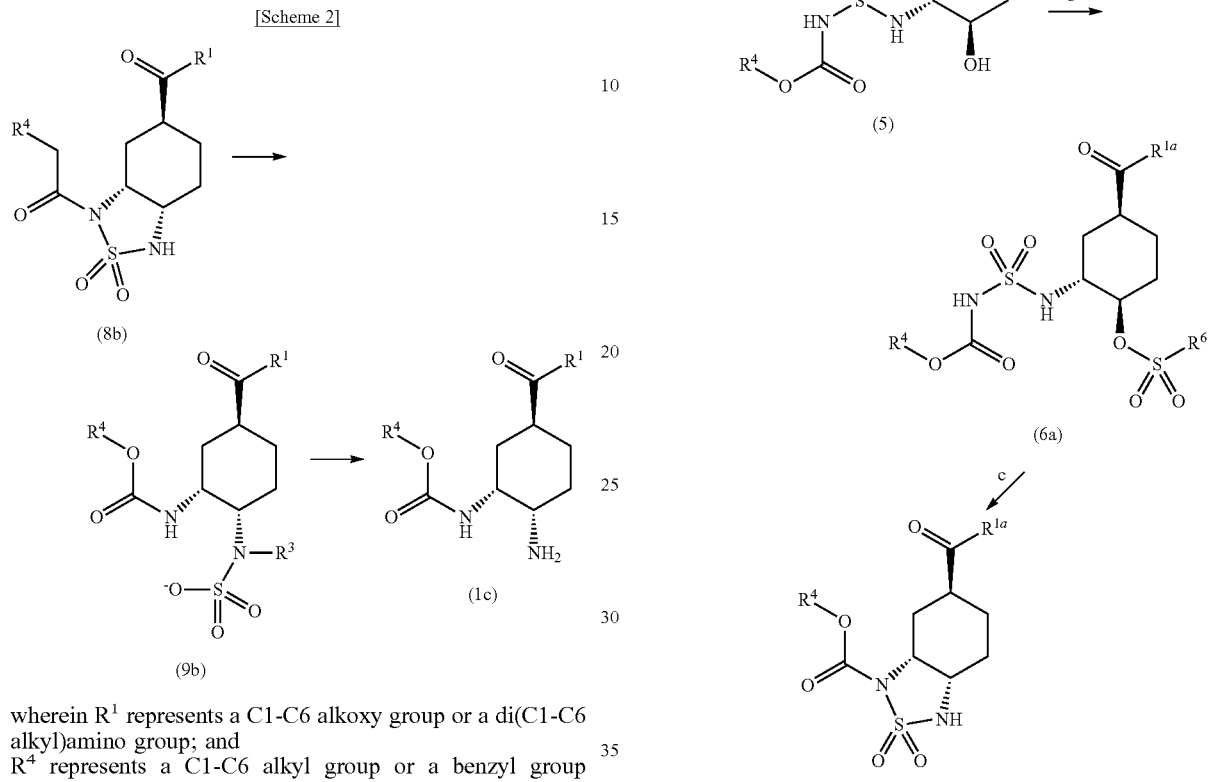

wherein $R^1$ represents a C1-C6 alkoxy group or a di(C1-C6 alkyl)amino group; and
$R^4$ represents a C1-C6 alkyl group or a benzyl group (wherein the benzyl group may have, on the benzene ring, one or two groups as substituents selected from the group consisting of a C1-C6 alkyl group, a C1-C6 alkoxy group, a nitro group, and a halogen atom).

In the [Scheme 2], $R^1$ is preferably a di(C1-C6 alkyl) amino group, and $R^4$ is preferably a C1-C6 alkyl group or a benzyl group.

In the reaction step shown in the [Scheme 2], the production method as explained in the above [Scheme 1] can be used. In addition, compound (9b) that is an intermediate can be isolated in the form of a salt, as described above.

Next, a more preferred embodiment of the present invention will be described.

As a specific example of producing the above described (3aR,7aS)-octahydro-2,1,3-benzothiadiazole derivative, a route for producing compound (8c), wherein $R^{1a}$ is a di(C1-C6 alkyl)amino group, is shown in the following [Scheme 3].

wherein $R^{1a}$ represents a di(C1-C6 alkyl)amino group;
$R^4$ represents a C1-C6 alkyl group or a benzyl group (wherein the benzyl group may have, on the benzene ring, one or two groups as substituents selected from the group consisting of a C1-C6 alkyl group, a C1-C6 alkoxy group, a nitro group, and a halogen atom); and
$R^6$ represents a C1-C6 alkyl group, a halo-C1-C6 alkyl group, or a phenyl group (wherein the phenyl group may have one or two groups as substituents selected from the group consisting of a C1-C6 alkyl group, a C1-C6 alkoxy group, a nitro group, and a halogen atom).

(Step a)

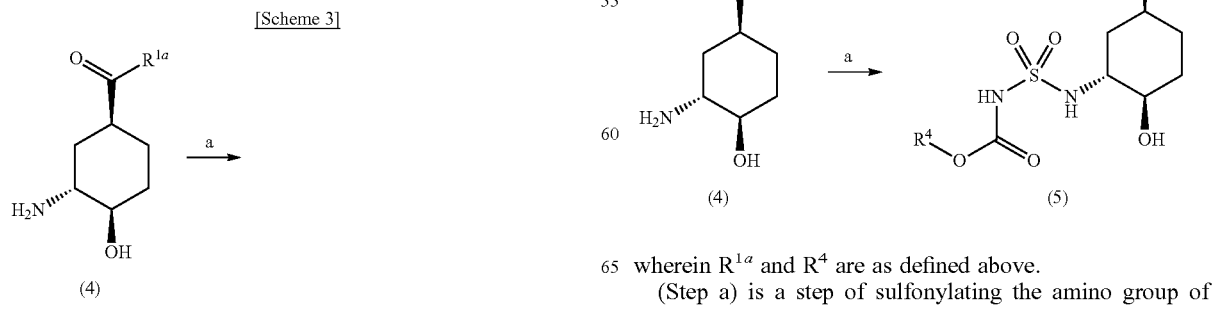

wherein $R^{1a}$ and $R^4$ are as defined above.

(Step a) is a step of sulfonylating the amino group of compound (4) (wherein a common production method will be described later) with compound (II) to produce compound (5). Moreover, a commercially available product may be directly used as such compound (II) ([reagent B]), or [solution A] that contains compound (II) may be prepared and used, as described below.

[Solution A]

Solution A is prepared by treating, in a solvent, a compound represented by the following formula (I):

wherein $R^4$ is as defined above, with chlorosulfonyl isocyanate (hereinafter also abbreviated as "CSI") and a tertiary amine.

Herein, $R^{1a}$ and $R^4$ in compound (4), compound (5) and compound (I) will be described.

$R^{1a}$ represents a di(C1-C6 alkyl)amino group, and it is preferably a di(methyl)amino group.

$R^4$ represents a C1-C6 alkyl group or a benzyl group (wherein the benzyl group may have, on the benzene ring, one or two groups as substituents selected from the group consisting of a C1-C6 alkyl group, a C1-C6 alkoxy group, a nitro group, and a halogen atom); and $R^4$ is preferably a C1-C6 alkyl group or a benzyl group, and is more preferably a tert-butyl group or a benzyl group.

Solution A can be prepared by treating commercially available chlorosulfonyl isocyanate that is known as a reagent used for dehydration reactions or conversion of a carboxy group to a cyano group with alcohol (I) represented by the following formula (I):

wherein $R^4$ is as defined above, and with a tertiary amine in a solvent. Preferred examples of the tertiary amine used in the preparation of solution A include triethylamine, diisopropylethylamine, 4-methylmorpholine, piperidine, pyrrolidine, tributylamine, 1,4-diazabicyclo[2.2.2]octane, and quinuclidine. Among others, triethylamine is particularly preferable. Solution A is prepared using alcohol (I) and the tertiary amine serving as a base in a solvent, and it contains, as a main component, the reaction reagent represented by the following formula (II):

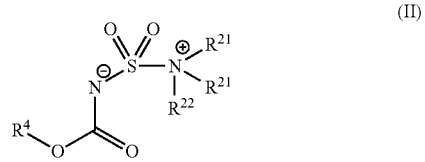

wherein $R^{21}$ and $R^{22}$ represent the following (a), (b) or (c):
(a) $R^{21}$ and $R^{22}$ are identical or different and each represent a C1-C6 alkyl group;
(b) $R^{22}$ represents a C1-C6 alkyl group, and the two $R^{21}$'s, together with the nitrogen atom to which the $R^{21}$'s bind, form a piperidine ring, a pyrrolidine ring or a 1,4-morpholine ring; or
(c) the two $R^{21}$'s and $R^{22}$, together with the nitrogen atom to which $R^{22}$ and the $R^{21}$'s bind, form a 1,4-diazabicyclo[2.2.2] octane ring or a quinuclidine ring; and
$R^4$ is as described above. Herein, compound (II), wherein $R^{21}$ and $R^{22}$ each represent an ethyl group and $R^4$ represents a methyl group, is commercially available as Burgess Reagent (see, for example, J. Indian Inst. Sci., 2001, 81, 461-476).

Examples of the solvent used in the preparation of solution A can include: ether solvents such as diethyl ether, di-n-propyl ether, diisopropyl ether, tetrahydrofuran, methyl tert-butyl ether or cyclopentyl methyl ether; ester solvents such as methyl acetate, ethyl acetate, propyl acetate, butyl acetate or phenyl acetate; halogenated hydrocarbon solvents such as dichloromethane, chloroform, carbon tetrachloride, dichloroethane or tetrachloroethane; aromatic hydrocarbon solvents such as benzene, chlorobenzene, toluene or xylene; nitrogen-containing solvents such as acetonitrile, N,N-dimethylformamide, N,N-dimethylacetamide or N-methyl pyrrolidone; ketone solvents such as acetone or methyl isobutyl ketone; and mixed solvents thereof. Preferred examples of the solvent include cyclopentyl methyl ether, tetrahydrofuran, ethyl acetate, chloroform, dichloromethane, toluene, acetonitrile, methyl isobutyl ketone, and mixed solvents thereof; and among others, acetonitrile is particularly preferable.

The amounts of the CSI, alcohol (I), and tertiary amine serving as a base used in the preparation of solution A are stoichiometrically preferably a molar equivalent ratio of approximately 1:0.95 to 1.05:2 to 4 (CSI:alcohol (I):tertiary amine).

The reaction temperature applied in the preparation of solution A is preferably room temperature or lower. The reaction time applied in the preparation of solution A is approximately 0.5 to 5 hours.

Alternatively, compound (5) can be produced by reacting an aqueous solution of compound (4) (a production method using an aqueous solution is exemplified herein) with the above described [solution A] at a temperature of approximately 0° C. At this time, a base may be added, and either an inorganic base or an organic base can be used herein, and of these, an inorganic base is preferable. Preferred examples of the inorganic base can include hydroxides and carbonates of alkaline metals or alkaline-earth metals. Among others, lithium hydroxide, sodium hydroxide, potassium hydroxide, sodium carbonate, and potassium carbonate are preferable, and it is preferable to use the base in the form of an aqueous solution containing such an inorganic base. With regard to the additive amount of such a base, it is preferable to add the base in an amount in which the reaction solution can maintain neutrality or basicity even after addition of [solution A]. The reaction temperature after addition of [solution A] is preferably from 0° C. to room temperature, and the reaction time required until termination of the reaction is approximately 0.5 to 5 hours.

After completion of the reaction, a mineral acid such as hydrochloric acid is added to the reaction solution, so that the pH is converted into a weakly acidic range. Thereafter, extraction is carried out with an organic solvent such as ethyl acetate to obtain compound (5).

(Step b)

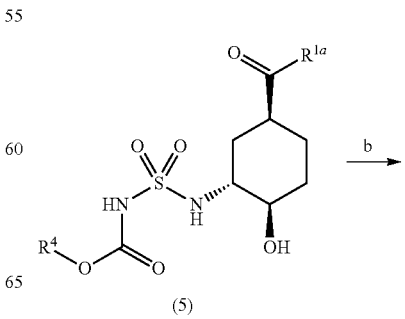

-continued

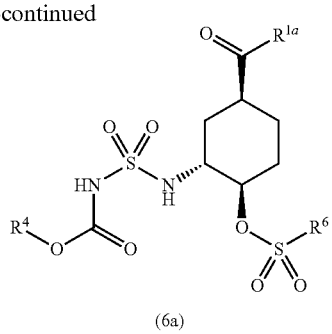

(6a)

wherein R⁶ represents a C1-C6 alkyl group, a halo-C1-C6 alkyl group, or a phenyl group (wherein the phenyl group may have one or two groups as substituents selected from the group consisting of a C1-C6 alkyl group, a C1-C6 alkoxy group, a nitro group, and a halogen atom); and $R^{1a}$ and $R^4$ are as defined above.

(Step b) is a step of treating, in the presence of a base, the compound (5) with a compound represented by the following formula (III):

$$R^6SO_2X \qquad (III)$$

wherein R⁶ is as defined above,
to produce compound (6a). As described above, R¹ in compound (5) and compound (6a) is particularly preferably a di(methyl)amino group; R⁴ is preferably a C1-C6 alkyl group or a benzyl group, and particularly preferably a tert-butyl group or a benzyl group; and R⁶ is preferably a methyl group, an ethyl group, a phenyl group, or a 4-methylphenyl group (p-tolyl group), and particularly preferably a methyl group.

In the (Step b), an organic solvent is preferably used as a reaction solvent. Examples of the organic solvent can include: ether solvents such as diethyl ether, diisopropyl ether, methyl tert-butyl ether (MTBE), tetrahydrofuran (THF), cyclopentyl methyl ether, dimethoxyethane or 1,4-dioxane; ester solvents such as methyl acetate, ethyl acetate, propyl acetate, butyl acetate or phenyl acetate; halogenated hydrocarbon solvents such as dichloromethane, chloroform, carbon tetrachloride, dichloroethane or tetrachloroethane; aromatic hydrocarbon solvents such as benzene, chlorobenzene, toluene or xylene; nitrogen-containing solvents such as acetonitrile; ketone solvents such as acetone or methyl isobutyl ketone; and mixed solvents thereof. Preferred examples of the solvent can include tetrahydrofuran, ethyl acetate, chloroform, dichloromethane, toluene, acetonitrile, methyl isobutyl ketone, and mixed solvents thereof; and among others, acetonitrile is particularly preferable.

Either an organic base or an inorganic base can be used as the base in the (Step b). Of these, an organic base is preferable, and examples of the organic base that can be used herein include: tertiary amines such as triethylamine, tributylamine or N,N-diisopropylethylamine; and other bases such as 1,8-diazabicyclo[5.4.0]undec-7-ene (DBU), 1,8-diazabicyclo[4.3.0]non-5-ene (DBN), dimethyl aniline or N-methylmorpholine.

Among these bases, tertiary amines such as triethylamine, N,N-diisopropylethylamine, N-methylmorpholine, pyridine, 2,6-lutidine or N-methylimidazole are preferable in the (Step b). Among others, triethylamine, N-methylmorpholine and 2,6-lutidine are particularly preferable.

In general, the amount of the base used may be stoichiometrically in the range of 0.8 to 5 molar equivalents, and preferably 1 to 1.5 molar equivalents, with respect to e compound (5).

As compound (III), methanesulfonyl chloride, ethanesulfonyl chloride, benzenesulfonyl chloride, p-toluenesulfonyl chloride and the like are preferable, and among these compounds, methanesulfonyl chloride is more preferable.

In general, the amount of compound (III) used may be stoichiometrically in the range of 0.8 to 3 molar equivalents, and preferably 1 to 1.5 molar equivalents, with respect to compound (5).

(Step b) is carried out at a reaction temperature of preferably 40° C. or lower, and more preferably approximately 0° C. The reaction time required until termination of the reaction is generally 0.5 to 5 hours.

(Step c)

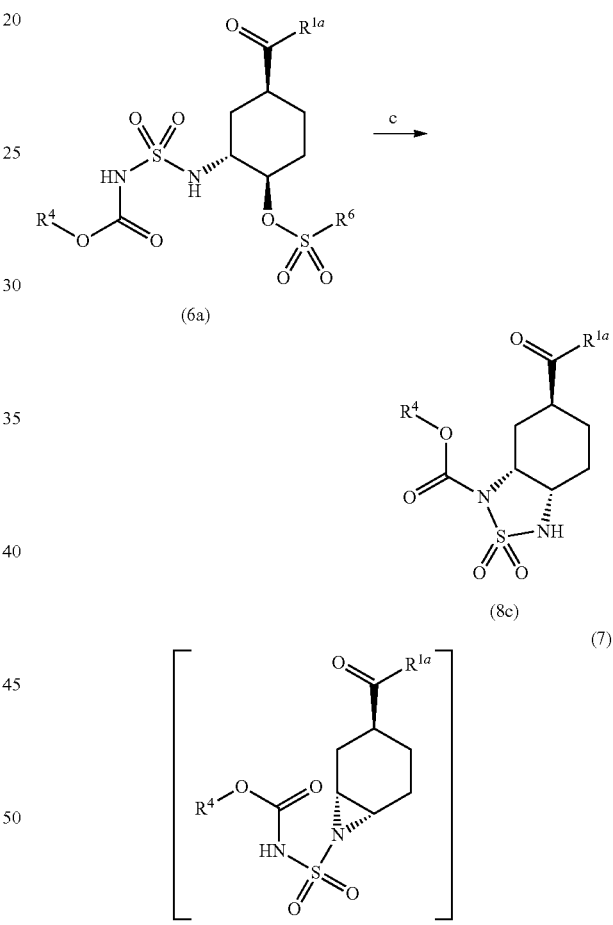

wherein $R^{1a}$ represents a di(C1-C6 alkyl)amino group;
R⁴ represents a C1-C6 alkyl group or a benzyl group (wherein the benzyl group may have, on the benzene ring, one or two groups as substituents selected from the group consisting of a C1-C6 alkyl group, a C1-C6 alkoxy group, a nitro group, and a halogen atom); and
R⁶ represents a C1-C6 alkyl group, a halo-C1-C6 alkyl group, or a phenyl group (wherein the phenyl group may have one or more groups as substituents selected from the group consisting of a C1-C6 alkyl group, a halo-C1-C6 alkyl group, a C1-C6 alkoxy group, a nitro group, and a halogen atom).

(Step c) is characterized in that compound (6a) is treated with a base, and in this step, compound (8c) having a (3aR,7aS)-octahydro-2,1,3-benzothiadiazole ring is produced by performing a stereoselective and regioselective intramolecular cyclization reaction. Herein, the fact that the reaction progresses via compound (7) that is an aziridine derivative serving as a reaction intermediate in the (Step c) has been supported by HPLC behavior and LC-MS results. That is to say, with regard to high regioselectivity in the (Step c), it is assumed that compound (7) that is considered to be chemico-kinetically preferential is obtained as a reaction intermediate by treating compound (6a) with the base, and the aziridine ring is then opened regioselectively, and thereafter, a ring closure for forming a thermodynamically stable 5-membered ring occurs again, so that compound (8c) can be selectively generated.

Since (Step c) is an intramolecular reaction, it is preferable to carry out this step in an organic solvent under dilution.

$R^{1a}$ is preferably a di(methyl)amino group; $R^4$ is preferably a C1-C6 alkyl group or a benzyl group, and is particularly preferably a tert-butyl group or a benzyl group; and $R^6$ is preferably a methyl group, an ethyl group, a phenyl group, or a 4-methylphenyl group (p-tolyl group), and is particularly preferably a methyl group.

Examples of the organic solvent used in the (Step c) include: ether solvents such as diethyl ether, diisopropyl ether, methyl tert-butyl ether (MTBE), tetrahydrofuran (THF), cyclopentyl methyl ether, dimethoxyethane or 1,4-dioxane; ester solvents such as methyl acetate, ethyl acetate, propyl acetate, butyl acetate or phenyl acetate; halogenated hydrocarbon solvents such as dichloromethane, chloroform, carbon tetrachloride, dichloroethane or tetrachloroethane; aromatic hydrocarbon solvents such as benzene, chlorobenzene, toluene or xylene; nitrogen-containing solvents such as acetonitrile; ketone solvents such as acetone or methyl isobutyl ketone; and mixed solvents thereof. Preferred examples of the solvent include tetrahydrofuran, chloroform, dichloromethane, toluene, acetonitrile, and mixed solvents thereof; and among others, acetonitrile is particularly preferable.

Either an organic base or an inorganic base can be used as the base in the (Step c). Of these, an organic base is preferable, and examples of the organic base that can be used herein can include: tertiary amines such as triethylamine or N,N-diisopropylethylamine; and other bases such as 1,8-diazabicyclo[5.4.0]undec-7-ene (DBU), 1,8-diazabicyclo[4.3.0]non-5-ene (DBN), (N,N-dimethyl)aniline or N-methylmorpholine.

In the present step, among these bases, tertiary amines such as triethylamine, N,N-diisopropylethylamine, N-methylmorpholine or pyridine are preferable. Among others, triethylamine is particularly preferable.

In general, the amount of the base used may be stoichiometrically in the range of 0.8 to 2 molar equivalents, and preferably 1 to 1.2 molar equivalents, with respect to compound (6a).

(Step c) can be carried out at a reaction temperature from room temperature to the boiling point of a solvent. The reaction temperature is preferably in the range of 70° C. to the boiling point of a solvent. The reaction time required until termination of the reaction is approximately 1 to 10 hours.

It has been explained that progression of the reaction via compound (7) that is an aziridine derivative is important in the (Step c) for the selective production of compound (8c) as a single reaction product, as described above. Accordingly, as shown in the following scheme, the present invention provides a method for selectively producing the compound represented by the following formula (8c) from the aziridine derivative represented by the following formula (7).

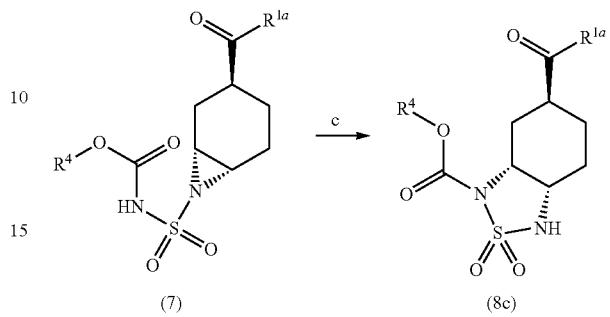

wherein $R^{1a}$ and $R^4$ are as defined above.

Herein, $R^{1a}$ is preferably a di(methyl)amino group; and $R^4$ is preferably a tert-butyl group or a benzyl group.

(Step d) and (Step e), in which a compound (1e) is produced from the compound (8c), are shown in the following [Scheme 4].

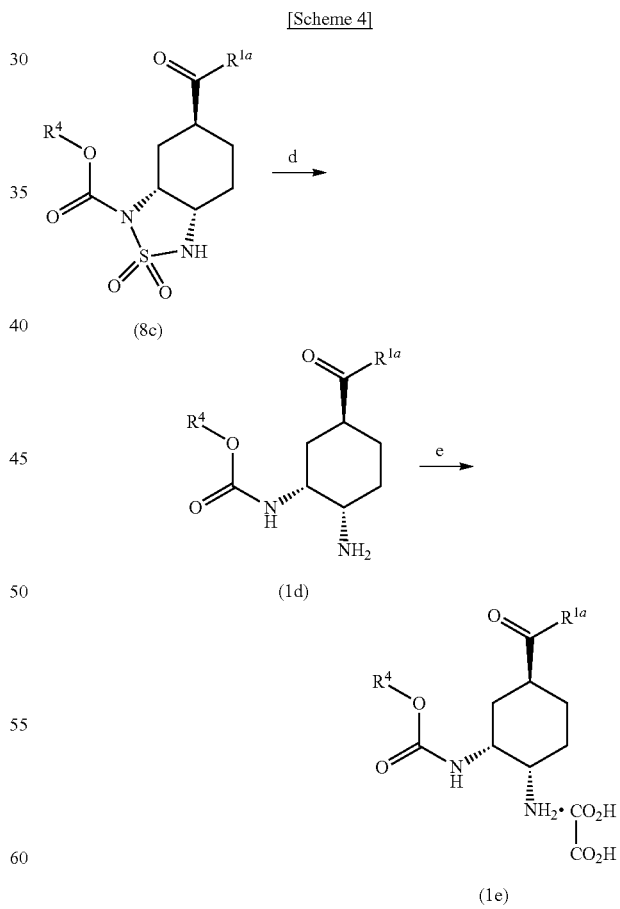

wherein $R^{1a}$ represents a di(C1-C6 alkyl)amino group; and $R^4$ represents a C1-C6 alkyl group or a benzyl group (wherein the benzyl group may have, on the benzene ring, one or two groups as substituents selected from the group consisting of a C1-C6 alkyl group, a C1-C6 alkoxy group, a nitro group, and a halogen atom).
(Step d)

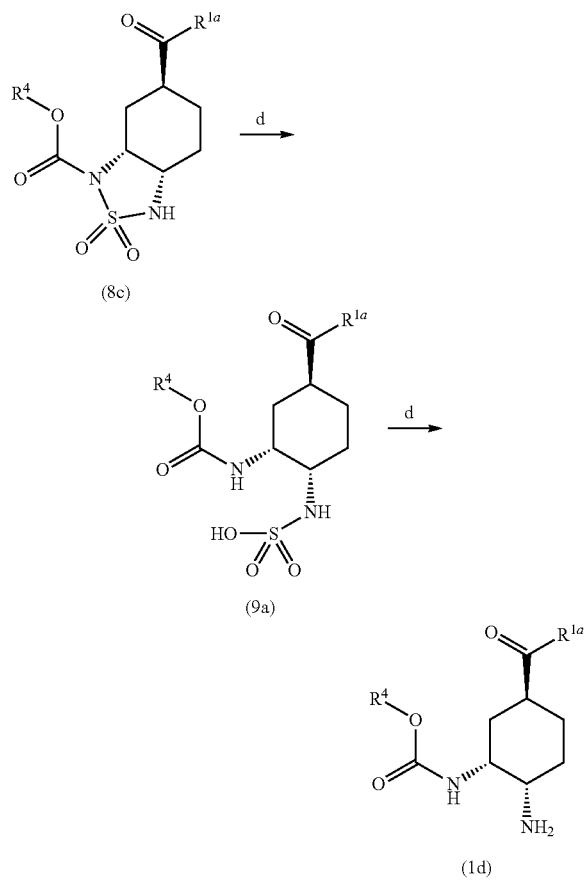

wherein $R^{1a}$ and $R^4$ are as defined above.

(Step d) is a step of cleaving two nitrogen-sulfur bonds in the thiadiazole ring to produce compound (1d). Herein, the "sulfonyl group (—S(O)$_2$—)" to be removed is considered to be a protecting group for two amino groups. Accordingly, as described above, the step can be carried out with reference to reaction conditions for deprotection regarding a "protecting group" for 1,2-diamino groups (see, for example, publications such as Organic Letters, 9(24), 4943-4945 (2007), Synlett, (6), 623-624 (1998), and Japanese Patent Laid-Open No. 2012-036181). Herein, in the desulfonylation reaction, a sulfamic acid derivative (9a), in which only one S—N bond is cleaved, is first generated, and compound (1d) is then generated by a further cleavage of the other S—N bond. However, it is possible to directly produce the desired compound (1d) or a salt thereof, or a hydrate thereof at a high yield under the below-mentioned production conditions, without isolating the compound (9a).

In a preferred embodiment of the (Step d), the compound (8c) is heated in a mixed solvent of water and a base to produce compound (1d).

Either an organic base or inorganic base can be used as a base. Of these, an organic base is preferable; pyridines such as pyridine, lutidine or collidine are more preferable; and pyridine is particularly preferable.

With regard to the additive ratio of water and base, the water and the base can be added at a ratio of 1:1 to 1:10 (V/V), and preferably at a ratio of approximately 1:1.5 to 1:5 (V/V).

With regard to the reaction temperature, the reaction can be carried out in the range of 50° C. to the boiling point of a solvent, and preferably in the range of 70° C. to 100° C.

The reaction time required until termination of the reaction is approximately 1 to 10 hours.

In addition, in the (Step d), an organic solvent can be used as a reaction auxiliary solvent. Examples of the organic solvent include: ether solvents such as dipropyl ether, diisopropyl ether, tetrahydrofuran, methyl tert-butyl ether or cyclopentyl methyl ether; halogenated hydrocarbon solvents such as chloroform, carbon tetrachloride, dichloroethane or tetrachloroethane; aromatic hydrocarbon solvents such as benzene, chlorobenzene, toluene or xylene; nitrogen-containing solvents such as acetonitrile, N,N-dimethylformamide, N,N-dimethylacetamide or N-methyl pyrrolidone; ketone solvents such as acetone or methyl isobutyl ketone; and mixed solvents thereof. Preferred examples can include tetrahydrofuran, chloroform, toluene, acetonitrile, and mixed solvents thereof.

Since compound (1d) that is a product is a basic compound, as a post-treatment performed after completion of the reaction, it is preferable to convert the reaction mixture to an alkaline mixture and then to extract the mixture with an organic solvent. In order to convert the reaction mixture to an alkaline mixture, an aqueous solution of the hydroxide or carbonate of an alkaline metal or alkaline-earth metal may be added to the reaction mixture. It is preferable to use lithium hydroxide, sodium hydroxide, potassium hydroxide, sodium carbonate or potassium carbonate in the form of an aqueous solution. Examples of the extraction solvent include: ether solvents such as diethyl ether, diisopropyl ether, methyl tert-butyl ether (MTBE), tetrahydrofuran (THF), cyclopentyl methyl ether, dimethoxyethane or 1,4-dioxane; ester solvents such as methyl acetate, ethyl acetate, propyl acetate, butyl acetate or phenyl acetate; halogenated hydrocarbon solvents such as dichloromethane, chloroform, carbon tetrachloride, dichloroethane or tetrachloroethane; and aromatic hydrocarbon solvents such as benzene, chlorobenzene, toluene or xylene.

On the other hand, after completion of the reaction, as an acid-added salt with sulfuric acid generated as a result of desulfonylation, the sulfate of compound (1d) precipitated from the reaction solution is filtered and washed, so that the product can be isolated and purified without performing the above described extraction procedures.
(Step e)

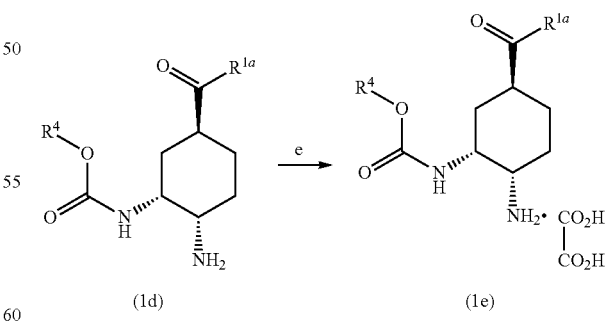

wherein $R^{1a}$ and $R^4$ are as defined above.

(Step e) is a step of treating compound (1d) produced in the (Step d) with oxalic acid to produce an oxalate of compound (1d), or a hydrate thereof that is compound (1e), and known methods disclosed, for example, in Publication 6 or WO 2012/002538 can be used.

Moreover, as described above, after completion of the reaction of the (Step d), as an acid-added salt with sulfuric acid generated as a result of desulfonylation, the sulfate of compound (1d) that has been precipitated from the reaction solution is filtered and is then washed, so that the product can be isolated and purified without performing the above described extraction procedures. Furthermore, such a sulfate of compound (1d) can be used in the below-mentioned production of compound (A-9), as in the case of compound (1e).

As shown in the following [Scheme 5], compound (4) [or an aqueous solution of the compound (4)] used in the above described (Step a) can be produced from compound (A-1) via compound (A-2) and compound (A-3) according to known methods.

[Scheme 5]

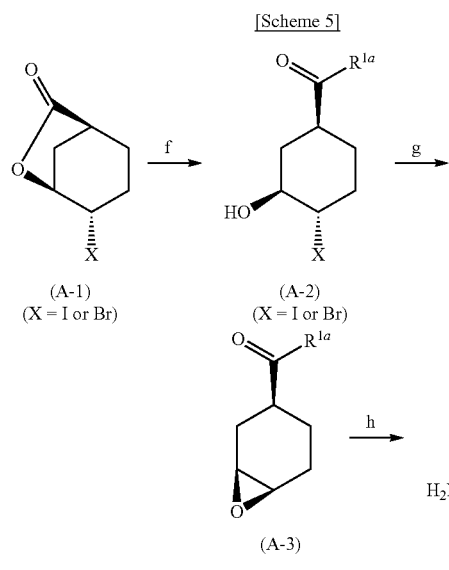

(A-1)
(X = I or Br)

(A-2)
(X = I or Br)

(A-3)

(4)

wherein $R^{1a}$ represents a di(C1-C6 alkyl)amino group; and X represents an iodine atom or a bromine atom.

Specific examples of producing the compound, wherein $R^{1a}$ represents a di(methyl)amino group, by (Step f) to (Step h) will be described as reference examples in the following Examples.

As a method for producing compound (X) that is a high-purity FXa inhibitor and compound (X-a) that is a mono-p-toluenesulfonate monohydrate of compound (X), using compound (A-9) produced from compound (1) of the present invention, known methods disclosed in Patent Literature 1 or Patent Literature 3 may be used, and specifically, the method is as described in the following scheme and the following examples.

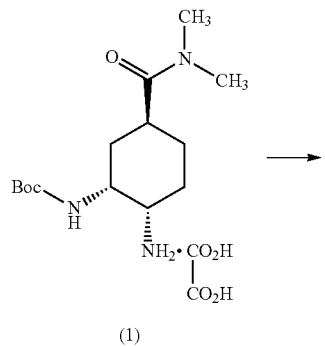

(1)

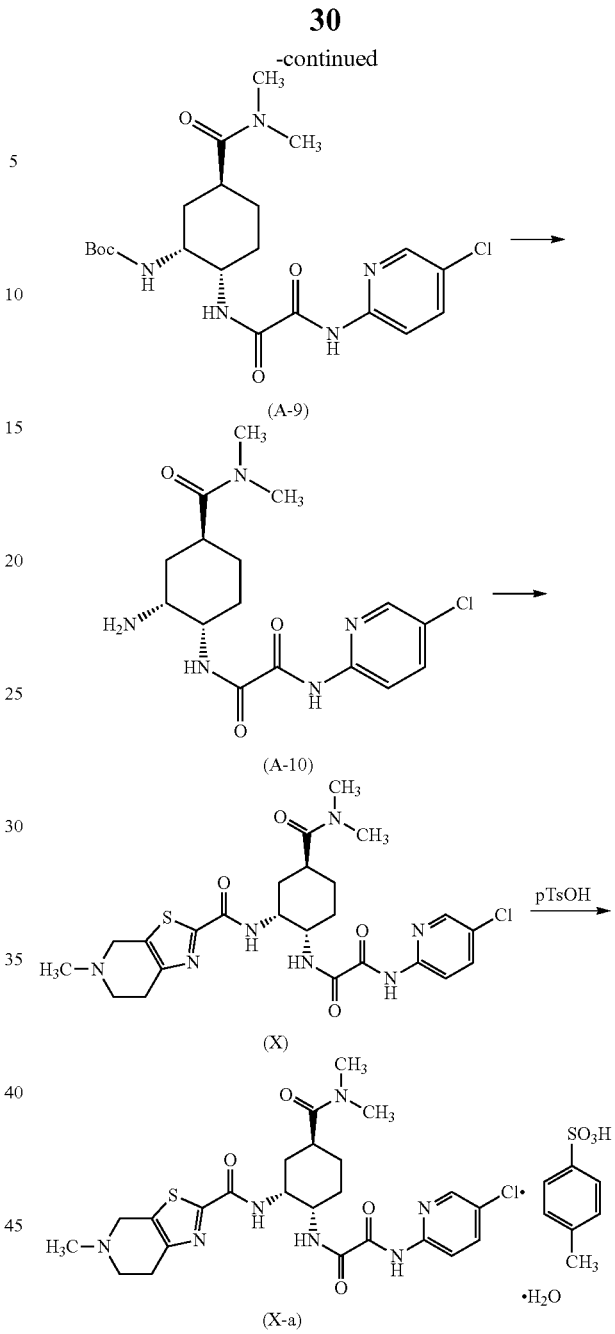

(A-9)

(A-10)

(X)

(X-a)

wherein Boc represents a tert-butoxycarbonyl group.

The present invention relates to a novel intermediate compound obtained in each of the following steps, as well as to the above described production method.

The present invention relates to a compound represented by the following formula (5):

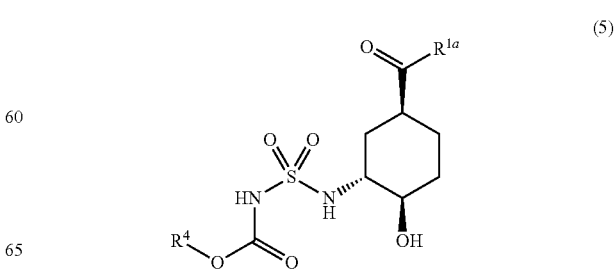

(5)

wherein $R^{1a}$ represents a di(C1-C6 alkyl)amino group; and

R⁴ represents a C1-C6 alkyl group or a benzyl group (wherein the benzyl group may have, on the benzene ring, one or two groups as substituents selected from the group consisting of a C1-C6 alkyl group, a C1-C6 alkoxy group, a nitro group, and a halogen atom).

Herein, as substituents in compound (5), $R^{1a}$ is preferably a di(methyl)amino group; and $R^4$ is preferably a C1-C6 alkyl group or a benzyl group; and more preferably a tert-butyl group or a benzyl group.

Moreover, the present invention relates to a compound represented by the following formula (6a):

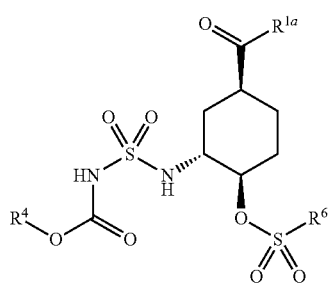

(6a)

wherein $R^{1a}$ represents a di(C1-C6 alkyl)amino group;
$R^4$ represents a C1-C6 alkyl group or a benzyl group (wherein the benzyl group may have, on the benzene ring, one or two groups as substituents selected from the group consisting of a C1-C6 alkyl group, a C1-C6 alkoxy group, a nitro group, and a halogen atom); and
$R^6$ represents a C1-C6 alkyl group, a halo-C1-C6 alkyl group, or a phenyl group (wherein the phenyl group may have one or two groups as substituents selected from the group consisting of a C1-C6 alkyl group, a C1-C6 alkoxy group, a nitro group, and a halogen atom).

Herein, as substituents in the compound represented by the above formula (6a), $R^{1a}$ is preferably a di(methyl)amino group; and
$R^4$ is preferably a C1-C6 alkyl group or a benzyl group; and particularly preferably a tert-butyl group or a benzyl group.
$R^6$ is preferably a C1-C6 alkyl group or a 4-methylphenyl group; and particularly preferably a methyl group.

Furthermore, the present invention relates to a compound represented by the following formula (8c):

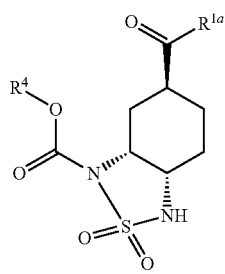

(8c)

wherein $R^{1a}$ represents a di(C1-C6 alkyl)amino group; and
$R^4$ represents a C1-C6 alkyl group or a benzyl group (wherein the benzyl group may have, on the benzene ring, one or two groups as substituents selected from the group consisting of a C1-C6 alkyl group, a C1-C6 alkoxy group, a nitro group, and a halogen atom).

Herein, as substituents in the compound represented by the above formula (8c), $R^{1a}$ is preferably a di(methyl)amino group; and
$R^4$ is preferably a C1-C6 alkyl group or a benzyl group; and particularly preferably a tert-butyl group or a benzyl group.

EXAMPLES

Next, the present invention will be described in detail with reference to the Examples. However, the present invention is not intended to be limited to these in any way.

Tetramethylsilane was used as the internal standard for the nuclear magnetic resonance (NMR) spectra. Abbreviations showing multiplicity represent s=singlet, d=doublet, t=triplet, q=quartet, m=multiplet, and brs=broad singlet.

Reference Example 1

(1S,4S,5S)-4-Bromo-6-oxabicyclo[3.2.1]octan-7-one

Under a nitrogen atmosphere, 1,3-dibromo-5,5-dimethylhydantoin (4) (11.6 g, 40.6 mol) was added to a solution of (S)-3-cyclohexene-1-carboxylic acid (R)-α-phenylethylamine salt (2-b) (10.0 g, 40.4 mmol) in acetonitrile (25 ml) that had been cooled on ice. The temperature of the reaction solution was increased to room temperature, and the reaction solution was then stirred for 2 hours. Thereafter, ethyl acetate (50 ml) and a 10% sodium thiosulfate aqueous solution (40 ml) were added to the reaction solution to separate it. The aqueous layer was extracted with ethyl acetate (50 ml), and the organic layers were gathered and were then washed with a 5% citric acid aqueous solution (40 ml). The resulting organic layer was washed with saturated saline (30 ml) and was then concentrated under reduced pressure. Thereafter, isopropyl alcohol (50 ml) was added to the residue, and the solvent was then concentrated under reduced pressure, so that the volume became 30 ml. The obtained slurry liquid was cooled to −10° C., and a precipitate was filtered and was then washed with ice-cooled isopropyl alcohol (10 ml) to obtain the title compound (6.9 g, yield: 84%).

Various spectrum data of the obtained compound were matched with the data described in the publication [M. Chini, et al., Tetrahedron, 48(3), 539-544, 1992].

Reference Example 2

(1S,3S,4S)-3-Hydroxy-4-bromo-N,N-dimethylcyclohexanecarboxamide

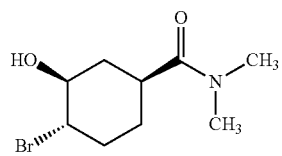

Ethyl acetate (1250 ml) was cooled to 5° C., and (1S,4S,5S)-4-bromo-6-oxabicyclo[3.2.1]octan-7-one (250 g) was then added thereto. Thereafter, a 50% dimethylamine aqueous solution (382 ml) was added to the above obtained solution, and the obtained mixture was then stirred for 14 hours. Thereafter, citric acid (234.2 g), 20% saline (500 ml), and ethyl acetate (625 ml) were added to the reaction mixture, and the obtained mixture was then stirred for 30 minutes, so that the organic layer was separated. Further, the aqueous layer was extracted with ethyl acetate (1875 ml). The organic layers were gathered, and the gathered organic layer was then concentrated to 1250 ml. Thereafter, water (500 ml) was added to the concentrated solution, and the mixed solution was then concentrated again to obtain the title compound (274.5 g, yield: 90%) in the form of an aqueous solution (625 ml).

Moreover, the present compound can also be isolated by filtrating crystals that have been precipitated from the above described ethyl acetate concentrated solution.

$^1$H-NMR (CDCl$_3$) δ: 1.60-1.78 (2H, m), 1.83-1.92 (2H, m), 2.18-2.24 (1H, m), 2.34-2.41 (1H, m), 2.81-2.90 (1H, m), 2.96 (3H, s), 3.07 (3H, s), 3.74-3.79 (1H, m), 4.03-4.08 (1H, m).

HRMS: calculated for C$_9$H$_{16}$BrNO$_2$, [M+H]$^+$: m/z 249.0364. found: m/z 249.0437.

HRMS (ESI$^+$): calculated for C$_9$H$_{16}$BrNO$_2$, [M+H]$^+$: m/z 250.0443; Found: m/z 250.0437.

Reference Example 3

(1S,3S,6R)—N,N-Dimethyl-7-oxabicyclo[4.1.0]heptane-3-carboxamide

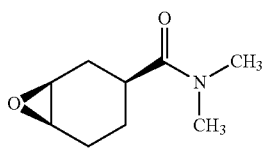

Methylene chloride (125 mL) was cooled to 0° C., and (1S,3S,4S)-3-hydroxy-4-bromo-N,N-dimethylcyclohexanecarboxamide (25 g) was then added thereto. Thereafter, a 25% sodium hydroxide aqueous solution (16 mL) was added to the above obtained solution, and the temperature of the obtained mixture was then increased to room temperature, followed by stirring the mixture for 3 hours. Thereafter, the organic layer was separated from the reaction mixture, and was then concentrated and dried to solidify. Thereafter, the resultant was dissolved in ethyl acetate (100 mL), and was then filtered over silica gel (25 g). The filtrate was concentrated and dried to solidify, and heptane (250 ml) was then added thereto, followed by crystallization, to obtain the title compound (13.91 g, yield: 82%).

$^1$H-NMR (CDCl$_3$) δ: 1.40-1.46 (1H, m), 1.56-1.67 (1H, m), 1.73-1.85 (1H, m), 1.96-2.03 (1H, m), 2.17-2.25 (2H, m), 2.41-2.49 (1H, m), 2.93 (3H, s), 3.03 (3H, s), 3.18-3.20 (2H, m).

Reference Example 4

(1S,3R,4R)-3-Amino-4-hydroxy-N,N-dimethylcyclohexanecarboxamide

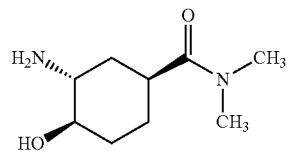

A 28% ammonia aqueous solution (1563 ml) was added to an aqueous solution (500 ml) of (1S,3S,4S)-3-hydroxy-4-bromo-N,N-dimethylcyclohexanecarboxamide (274.5 g), and the obtained solution was then heated to 40° C., followed by stirring the reaction solution for 8 hours. Thereafter, the reaction solution was further stirred at room temperature for 6 hours. Thereafter, 48% sodium hydroxide (67.3 ml) was added to the reaction mixture, and the obtained mixture was then concentrated to 500 ml to obtain the title compound (184.0 g, yield: 81%) in the form of an aqueous solution (572 g).

Reference Example 5

(1S,3R,4R)-3-Amino-4-hydroxy-N,N-dimethylcyclohexanecarboxamide

A 28% ammonia aqueous solution (125 mL) was added to an aqueous solution (50 mL) of (1S,3S,4S)-3-hydroxy-4-bromo-N,N-dimethylcyclohexanecarboxamide (21.84 g), and the obtained solution was then heated to 40° C., followed by stirring the reaction solution for 8 hours. Thereafter, the reaction solution was further stirred at room temperature for 6 hours. Thereafter, the reaction mixture was concentrated to 50 mL to obtain 14.33 g of the title compound (yield: 79%) in the form of an aqueous solution (49 g).

Reference Example 6

(1S,3R,4R)-3-Amino-4-hydroxy-N,N-dimethylcyclohexanecarboxamide (1S,4S,5S)-4-Bromo-6-oxabicyclo[3.2.1]octan-7-one (200 g) was added to ethyl acetate (1000 ml), and the obtained solution was then cooled to 5° C. Thereafter, a 50% dimethylamine aqueous solution (305.7 ml) was added to the reaction solution, and the obtained mixture was then stirred for 14 hours. Thereafter, a mixed solution of citric acid (131.17 g), common salt (92.00 g) and water (324 ml) was added to the reaction solution, and the obtained mixture was then heated to 30° C. The reaction solution was stirred for 30 minutes, and thereafter, it was left at rest, so that the organic layer was separated. Further, the aqueous layer was extracted with ethyl acetate (800 ml) again. The organic layers were gathered, and the gathered organic layer was then concentrated to 1000 ml. Water (400 ml) was added to the concentrated solution, and the thus mixed solution was concentrated again to obtain an aqueous solution (500 ml) of (1S,3S,4S)-3-hydroxy-4-bromo-N,N-dimethylcyclohexanecarboxamide. To this aqueous solution (500 ml), a 28% ammonia aqueous solution (1247 ml) and a 25% sodium hydroxide aqueous solution (123 ml) were added, and the obtained solution was then heated to 40° C., followed by stirring the reaction solution for 6 hours. Thereafter, the reaction solution was concentrated to 1000 ml to obtain an aqueous solution containing the title compound (147.52 g, yield: 81%).

Reference Example 7 tert-Butyl {(1R,2S,5S)-2-amino-5-[(dimethylamino)carbonyl]cyclohexyl}carbamate oxalate (1) (the production method described in the pamphlet of International Publication No. WO 2007/032498)

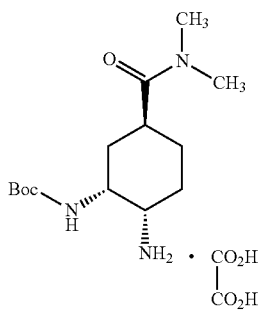
(1)

wherein Boc represents a tert-butoxycarbonyl group.

Sodium azide (7.14 g) and dodecylpyridinium chloride (7.80 g) were added to a solution of (1R,2R,4S)-2-[(tert-butoxycarbonyl)amino]-4-[(dimethylamino)carbonyl]cyclohexylmethanesulfonate (A-6) (20.0 g) in toluene (100 ml) at room temperature. The mixed solution was stirred at 60° C. for 72 hours and then allowed to cool to room temperature. To the reaction solution, water was added, and the organic layer was separated. The organic layer was washed with a saturated aqueous solution of sodium bicarbonate and water, and then, the solvent was distilled off.

To the residue, methanol, and then 7.5% Pd—C and ammonium formate were added, and the mixture was stirred at 40° C. for 1 hour. Pd—C was filtered off, and then, the solvent was concentrated under reduced pressure. To this residue, aqueous acetonitrile (200 ml) and anhydrous oxalic acid (4.94 g) were added, and the mixture was stirred at room temperature for 17 hours. The precipitated crystals were collected by filtration. The obtained crystals were added to acetonitrile (200 ml), and the mixture was stirred at 40° C. for 24 hours. The precipitated crystals were collected by filtration and dried to obtain the title compound (1) (12.7 g).

$^1$H-NMR (D$_2$O) δ: 1.30 (9H, s), 1.37-1.49 (2H, m), 1.60-1.66 (1H, m), 1.72-1.83 (3H, m), 2.77 (3H, s) 2.80-2.83 (1H, m), 2.96 (3H, m), 3.30-3.33 (1H, m), 4.10 (1H, br).

Elemental analysis: C$_{16}$H$_{29}$N$_3$O$_7$.

Theoretical: C, 50.70%; H, 7.75%; N, 10.96%.

Found: C, 51.19%; H, 7.79%; N, 11.19%.

Reference Example 8

Ethyl 2-[(5-chloropyridin-2-yl)amino]-2-oxoacetate monohydrochloride (A-8) (the production method described in the pamphlet of International Publication No. WO 2007/032498)

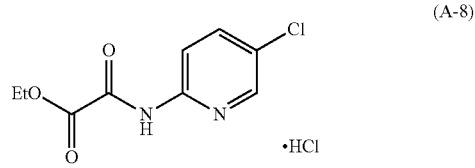 [SMILES: CCOC(=O)C(=O)Nc1ccc(Cl)cn1 ; Cl]

Ethyl oxalyl chloride (11.7 g) was added to a suspension of 2-amino-5-chloropyridine (10.0 g) in acetonitrile (120 ml) at 50° C., and the mixture was stirred at this temperature for 2 hours. The reaction solution was cooled, and crystals were collected by filtration at 10° C., washed with acetonitrile (40 ml), and then dried under reduced pressure to obtain the title compound (A-8) (19.7 g).

Reference Example 9 tert-Butyl(1R,2S,5S)-2-({2-[(5-chloro-2-pyridin-2-yl)amino]-2-oxoacetyl}amino)-5-(dimethylaminocarbonyl)cyclohexylcarbamate (A-9) (the production method described in the pamphlet of International Publication No. WO 2007/032498)

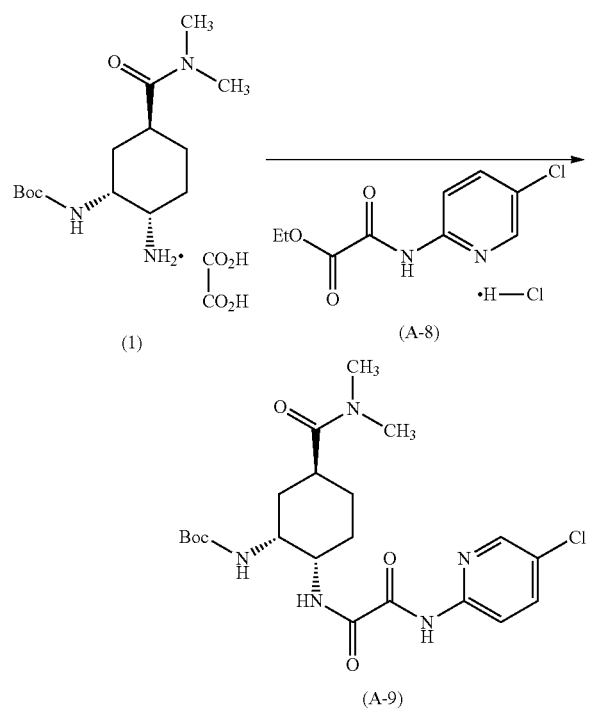

wherein Boc represents a tert-butoxycarbonyl group.

Triethylamine (169 ml) was added to a suspension of tert-butyl(1R,2S,5S)-2-amino-5-(dimethylaminocarbonyl)cyclohexylcarbamate monooxalate (1) (100.1 g) in acetonitrile (550 ml) at 60° C. Ethyl 2-[(5-chloropyridin-2-yl)amino]-2-oxoacetate monohydrochloride (A-8) (84.2 g) was added thereto at this temperature, and the mixture was stirred for 6 hours and then stirred at room temperature for 16 hours. To the reaction solution, water was added, and the mixture was stirred at 10° C. for 1.5 hours. Then, crystals were collected by filtration to obtain the title compound (A-9) (106.6 g).

$^1$H-NMR (CDCl$_3$) δ: 1.25-1.55 (2H, m), 1.45 (9H, s), 1.60-2.15 (5H, m), 2.56-2.74 (1H, brs), 2.95 (3H, s), 3.06 (3H, s), 3.90-4.01 (1H, m), 4.18-4.27 (1H, m), 4.70-4.85 (0.7H, br), 5.70-6.00 (0.3H, brs), 7.70 (1H, dd, J=8.8, 2.4 Hz), 7.75-8.00 (1H, br), 8.16 (1H, brd, J=8.8 Hz), 8.30 (1H, d, J=2.4 Hz), 9.73 (1H, s).

Reference Example 10

N$^1$-(5-Chloropyridin-2-yl)-N$^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide (X) (the production method described in the pamphlet of International Publication No. WO 2007/032498)

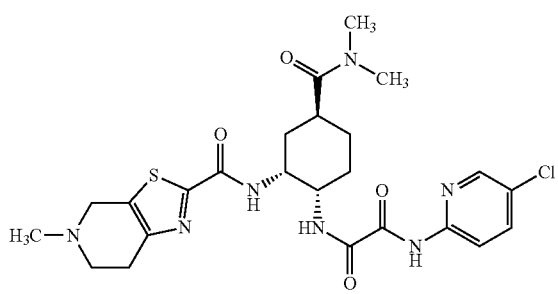

(X)

Methanesulfonic acid (66 ml) was added to a suspension of tert-butyl[(1R,2S,5S)-2-({[(5-chloropyridin-2-yl)amino](oxo)acetyl}amino)-5-(dimethylaminocarbonyl)cyclohexyl]carbamate (A-9) (95.1 g) in acetonitrile (1900 ml) at room temperature, and the mixture was stirred at this temperature for 2 hours. To the reaction solution, triethylamine (155 ml), 5-methyl-4,5,6,7-tetrahydro[1,3]thiazolo[5,4-c]pyridine-2-carboxylic acid hydrochloride (52.5 g), 1-hydroxybenzotriazole (33.0 g), and 1-ethyl-3-(3-dimethylaminopropyl)carbodiimide hydrochloride (46.8 g) were added under ice cooling, and the mixture was stirred at room temperature for 16 hours. Triethylamine and water were added thereto, and the mixture was stirred for 1 hour under ice cooling. Then, crystals were collected by filtration to obtain the title compound (X) (103.2 g).

$^1$H-NMR (CDCl$_3$) δ: 1.60-1.98 (3H, m), 2.00-2.16 (3H, m), 2.52 (3H, s), 2.78-2.90 (3H, m), 2.92-2.98 (2H, m), 2.95 (3H, s), 3.06 (3H, s), 3.69 (1H, d, J=15.4 Hz), 3.75 (1H, d, J=15.4 Hz), 4.07-4.15 (1H, m), 4.66-4.72 (1H, m), 7.40 (1H, dd, J=8.8, 0.6 Hz), 7.68 (1H, dd, J=8.8, 2.4 Hz), 8.03 (1H, d, J=7.8 Hz), 8.16 (1H, dd, J=8.8, 0.6 Hz), 8.30 (1H, dd, J=2.4, 0.6 Hz), 9.72 (1H, s).

MS (ESI) m/z: 548 (M+H)$^+$.

Reference Example 11

N$^1$-(5-Chloropyridin-2-yl)-N$^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide mono-p-toluenesulfonate monohydrate (X-a) (the production method described in the pamphlet of International Publication No. WO 2007/032498)

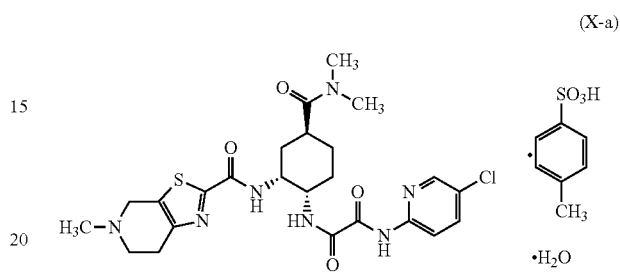

(X-a)

N$^1$-(5-Chloropyridin-2-yl)-N$^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide (X) (6.2 g) was dissolved in methylene chloride (120 ml). To the solution, a 1 mol/L solution of p-toluenesulfonic acid in ethanol (11.28 ml) was added, and the solvent was distilled off. To the residue, 15% aqueous ethanol (95 ml) was added, and the mixture was dissolved by stirring at 60° C. Then, the mixture was cooled to room temperature and stirred for 1 day. The precipitated crystals were collected by filtration, washed with ethanol, and then dried under reduced pressure at room temperature for 2 hours to obtain the title compound (X-a) (7.4 g).

$^1$H-NMR (DMSO-d$_6$) δ: 1.45-1.54 (1H, m), 1.66-1.78 (3H, m), 2.03-2.10 (2H, m), 2.28 (3H, s), 2.79 (3H, s), 2.91-3.02 (1H, m), 2.93 (3H, s), 2.99 (3H, s), 3.13-3.24 (2H, m), 3.46-3.82 (2H, m), 3.98-4.04 (1H, m), 4.43-4.80 (3H, m), 7.11 (2H, d, J=7.8 Hz), 7.46 (2H, d, J=8.2 Hz), 8.01 (2H, d, J=1.8 Hz), 8.46 (1H, t, J=1.8 Hz), 8.75 (1H, d, J=6.9 Hz), 9.10-9.28 (1H, br), 10.18 (1H, br), 10.29 (1H, s).

MS (ESI) m/z: 548 (M+H)$^+$.

Elemental analysis: C$_{24}$H$_{30}$ClN$_7$O$_4$S·C$_7$H$_8$O$_3$S·H$_2$O
Theoretical: C, 50.43; H, 5.46; N, 13.28, Cl; 4.80, S; 8.69.
Found: C, 50.25; H, 5.36; N, 13.32, Cl; 4.93, S; 8.79.
mp (dec.): 245° C.-248° C.

Example 1 tert-Butyl {[(1R,2R,5S)-5-(Dimethylcarbamoyl)-2-hydroxycyclohexyl]sulfamoyl}carbamate

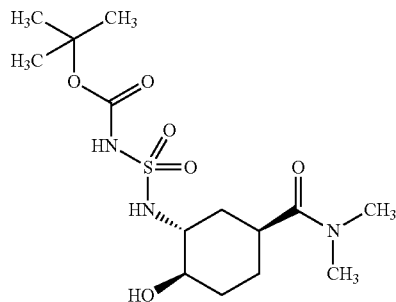 [SMILES: CN(C)C(=O)[C@H]1CC[C@@H](O)[C@H](NS(=O)(=O)NC(=O)OC(C)(C)C)C1]

tert-Butyl alcohol (9.2 mL) was added to methylene chloride (70 mL), and the obtained solution was then cooled to approximately 0° C. Chlorosulfonyl isocyanate (8.34 mL) was added dropwise to the reaction solution over approximately 15 minutes, and the thus obtained solution was then stirred for approximately 5 minutes. Thereafter, triethylamine (28.7 mL) was added dropwise to the reaction mixture over approximately 20 minutes to prepare a Burgess-type reagent.

To an aqueous solution (34 g) of (1S,3R,4R)-3-amino-4-hydroxy-N,N-dimethylcyclohexanecarboxamide (10.0 g) prepared by the same method as that in Reference Example 5, a 48% sodium hydroxide aqueous solution (11.2 mL) was added, and the obtained solution was then stirred for approximately 30 minutes. Thereafter, the Burgess-type reagent prepared by the above described method was added to the reaction mixture over approximately 5 minutes, and the thus prepared solution was washed with methylene chloride (5 mL), followed by dropwise addition, and the obtained mixture was stirred for 2 hours. Thereafter, a 6 mol/L hydrochloric acid solution was added to the reaction mixture, so that the pH of the mixture was adjusted to pH 1.5. Then, the organic layer was separated. The aqueous layer was extracted with methylene chloride (100 mL) again. The organic layers were gathered, and the gathered organic layer was washed with 20% saline (50 mL) and was then concentrated and dried to solidify. Ethyl acetate (300 mL) was added to the obtained residue, and the obtained solution was then concentrated to approximately 100 mL. The obtained concentrated solution was cooled to approximately 0° C., and it was then stirred for approximately 30 minutes. Thereafter, the precipitated crystals were collected by filtration, and were then dried under reduced pressure. The obtained crude crystals were added to water (30 mL), and the obtained solution was then stirred. The mixture was filtered and was then washed with water. The obtained crystals were dried under reduced pressure to obtain 13.26 g of the title compound (yield: 68%) in the form of crystals.

$^1$H-NMR (CDCl$_3$) δ: 1.48 (9H, s), 1.49-1.62 (2H, m), 1.72-1.80 (1H, m), 1.83-1.90 (2H, m), 2.31 (1H, td, J=5.0, 13.4 Hz), 2.86-2.91 (2H, m), 2.93 (3H, s), 3.04 (3H, s), 3.55 (1H, m), 3.84-3.89 (1H, m), 5.32 (1H, d, J=6.9 Hz), 8.12 (1H, s).

HRMS (ESI$^-$): calculated for C$_{14}$H$_{27}$N$_3$O$_6$S, [M–H]$^-$: m/z 364.1542. Found m/z 364.1549.

Example 2 tert-Butyl {[(1R,2R,5S)-5-(Dimethylcarbamoyl)-2-hydroxycyclohexyl]sulfamoyl}carbamate tert-Butyl alcohol (51 ml) was added to acetonitrile (600 ml), and the obtained solution was then cooled to approximately 0° C. Thereafter, chlorosulfonyl isocyanate (46.3 ml) was added dropwise to the reaction solution over approximately 20 minutes, and the obtained mixture was then stirred for approximately 15 minutes. Thereafter, triethylamine (156.3 ml) was added dropwise to the reaction mixture over approximately 30 minutes, and the obtained mixture was further stirred for approximately 30 minutes to prepare a Burgess-type reagent.

An aqueous solution (229 g) of (1S,3R,4R)-3-amino-4-hydroxy-N,N-dimethylcyclohexanecarboxamide (73.6 g) prepared by the same method as that described in Reference Example 4 was cooled to approximately 0° C., and a 48% sodium hydroxide aqueous solution (40.4 ml) was then added to the reaction solution, followed by stirring the mixture for approximately 30 minutes. Thereafter, the Burgess-type reagent prepared by the above described method was added dropwise to the reaction mixture, and the thus prepared solution was then washed with acetonitrile (75 ml), followed by dropwise addition, and the obtained mixture was stirred for approximately 1 hour. Thereafter, a 6 mol/l hydrochloric acid solution (211 ml) was added to the reaction mixture, so that the pH of the mixture was adjusted to pH 4. Then, acetonitrile was distilled off. To the concentrated reaction mixture, ethyl acetate (750 ml) and water (75 ml) were added, and the obtained mixture was intensively stirred, and the organic layer was then separated. The aqueous layer was extracted with ethyl acetate (750 ml) again. The gathered organic layers were washed with 22% saline (380 ml) and were then concentrated. To the obtained residue, acetonitrile (750 ml) was added, and the obtained mixture was then concentrated. Acetonitrile (750 ml) was added to the residue again, and the obtained mixture was then concentrated to obtain the title compound (138.5 g, yield: 96%) in the form of an acetonitrile slurry liquid (300 ml). The spectra of a resulting product partially isolated from the present liquid, which were obtained using various devices, were matched with those obtained in Example 1.

Example 3 tert-Butyl {[(1R,2R,5S)-5-(dimethylcarbamoyl)-2-hydroxycyclohexyl]sulfamoyl}carbamate tert-Butyl alcohol (5.56 ml) was added to acetonitrile (60 ml), and the obtained solution was then cooled to approximately 0° C. Chlorosulfonyl isocyanate (5.06 ml) was added dropwise to the reaction solution over approximately 10 minutes, and the obtained mixture was then stirred for approximately 15 minutes. Thereafter, triethylamine (17.1 ml) was added dropwise to the reaction mixture over approximately 15 minutes, and the obtained mixture was then stirred for approximately 30 minutes to prepare a Burgess-type reagent.

A 25% sodium hydroxide aqueous solution (9.14 ml) was added to an aqueous solution (46.5 g) of (1S,3R,4R)-3-amino-4-hydroxy-N,N-dimethylcyclohexanecarboxamide (6.43 g) prepared by the same method as that in Reference Example 4, and the obtained mixture was then stirred for approximately 30 minutes. This mixture was added dropwise into the Burgess-type reagent prepared by the above described method over approximately 10 minutes, and after completion of the dropwise addition, the obtained mixture was stirred for 3 hours. Thereafter, acetonitrile was distilled off from the reaction mixture, and ethyl acetate (75 ml) and citric acid (4.21 g) were then added to the residue, so that the pH of the mixture was adjusted to pH 4. Thereafter, the mixture was intensively stirred, and the organic layer was then separated. The aqueous layer was extracted with ethyl acetate (75 ml) again. The gathered organic layers were washed with 20% saline (38 ml) and were then concentrated. To the obtained residue, acetonitrile (75 ml) was added, and the obtained mixture was then concentrated. Acetonitrile (75 ml) was added to the residue again, and the obtained mixture was then concentrated to obtain the title compound (12.1 g, yield: 96%) in the form of an acetonitrile solution (30 ml). The spectra of a resulting product partially isolated from the present liquid, which were obtained using various devices, were matched with those obtained in Example 1.

Example 4

Benzyl {[(1R,2R,5S)-5-(dimethylcarbamoyl)-2-hydroxycyclohexyl]sulfamoyl}carbamate

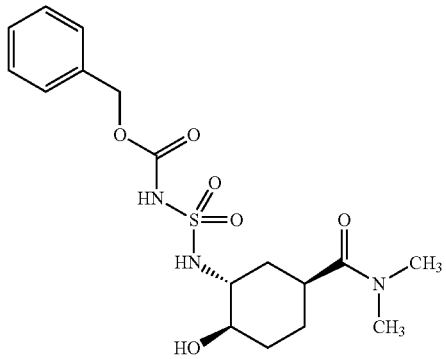 [SMILES: CN(C)C(=O)[C@H]1CC[C@@H](O)[C@H](NS(=O)(=O)NC(=O)OCc2ccccc2)C1]

Chlorosulfonyl isocyanate (1.36 ml) was added to methylene chloride (15 ml), and the obtained solution was then cooled to approximately 0° C. Benzyl alcohol (1.36 ml) was added dropwise to the reaction solution over approximately 15 minutes, and the obtained mixture was then stirred for 5 minutes. Thereafter, triethylamine (4.42 ml) was added dropwise to the reaction mixture over approximately 20 minutes to prepare a Burgess-type reagent.

A 6 mol/l hydrochloric acid solution (15.00 mL) was added to tert-butyl {(1R,2R,5S)-5-[(dimethylamino)carbonyl]-2-hydroxycyclohexyl}carbamate (Example 12 in International Publication No. WO 2007/032498) (3.00 g), and the obtained mixture was then stirred for approximately 30 minutes. Thereafter, a 48% sodium hydroxide aqueous solution (9.7 ml) was added to the reaction mixture, and the prepared Burgess-type reagent was then added thereto using methylene chloride (5 mL) over approximately 5 minutes. The thus obtained mixture was further stirred at room temperature for approximately 2 hours.

After completion of the reaction had been confirmed, a 6 mol/l hydrochloric acid solution was added to the reaction solution, so that the pH of the solution was adjusted to pH 1.5, and the organic layer was then separated. The aqueous layer was extracted with methylene chloride (100 mL) again. The organic layers were gathered, and the gathered organic layer was purified by silica gel column chromatography to obtain 2.22 g of the title compound (yield: 53%) in the form of an oily compound.

$^1$H-NMR (CDCl$_3$) δ: 1.38-1.55 (2H, m), 1.62-1.72 (1H, m), 1.73-1.82 (2H, m), 2.15-2.21 (1H, m), 2.74-2.79 (1H, m), 2.85 (3H, s), 2.94 (3H, s), 3.42-3.49 (1H, m), 3.82-3.91 (1H, m), 5.12 (1H, d, J=12.0 Hz), 5.15 (1H, d, J=12.0 Hz), 7.28-7.36 (6H, m).

Example 5

(1R,2R,4S)-2-{[(tert-Butoxycarbonyl) sulfamoyl] amino}-4-(dimethylcarbamoyl)cyclohexyl methanesulfonate

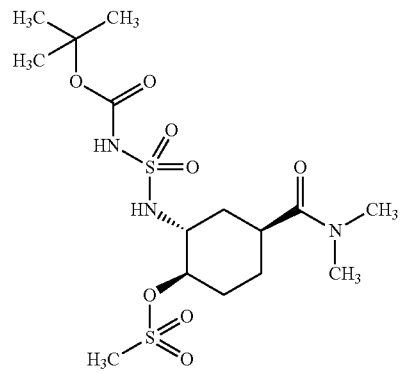 [SMILES: CN(C)C(=O)[C@H]1CC[C@@H](OS(C)(=O)=O)[C@H](NS(=O)(=O)NC(=O)OC(C)(C)C)C1]

Acetonitrile (460 ml) and triethylamine (87.0 ml) were added to a solution of tert-butyl {[(1R,2R,5S)-5-(dimethylcarbamoyl)-2-hydroxycyclohexyl]sulfamoyl}carbamate (138.5 g) in acetonitrile (300 ml), and the obtained solution was then cooled to approximately 0° C. Methanesulfonyl chloride (38.5 ml) was added dropwise to the reaction solution, and the obtained mixture was then stirred for approximately 30 minutes. Thereafter, water (610 ml) was added to the reaction mixture, and the obtained mixture was stirred for approximately 30 minutes. Subsequently, water (930 ml) was added to the reaction mixture, and the obtained mixture was further stirred for approximately 3 hours. Thereafter, the precipitated solid was collected by filtration and was then washed with 27.5% aqueous acetonitrile (300 ml). The obtained solid was dried under reduced pressure to obtain the title compound (138.5 g, yield: 82%).

$^1$H-NMR (CDCl$_3$) δ: 1.49 (9H, s), 1.61-1.69 (2H, m), 1.84-1.91 (1H, m), 1.98-2.05 (2H, m), 2.35 (1H, ddd, J=4.8, 8.9, 14.4 Hz), 2.82-2.86 (1H, m), 2.94 (3H, s), 3.06 (3H, s), 3.10 (3H, s), 3.99 (1H, m), 4.72-4.75 (1H, m), 5.37 (1H, d, J=5.5 Hz), 7.39 (1H, s).

HRMS (ESI$^-$): calculated for C$_{15}$H$_{29}$N$_3$O$_8$S$_2$, M–H$^-$ m/z 442.1318.

Found m/z 442.1326.

Example 6

(1R,2R,4S)-2-{[(tert-Butoxycarbonyl) sulfamoyl] amino}-4-(dimethylcarbamoyl)cyclohexyl methanesulfonate Acetonitrile (30 ml) was added to a solution of tert-butyl {[(1R,2R,5S)-5-(dimethylcarbamoyl)-2-hydroxycyclohexyl]sulfamoyl}carbamate (12.1 g) in acetonitrile (30 ml), and the obtained solution was then cooled to approximately 0° C. Thereafter, methanesulfonyl chloride (3.77 ml) was added to the reaction solution. N-methylmorpholine (6.81 ml) was added dropwise to the reaction mixture, and the obtained mixture was then stirred for approximately 3 hours. Thereafter, water (61 ml) was added to the reaction mixture, and a 6 mol/l hydrochloric acid solution was then added thereto to adjust the pH of the mixture to pH 3. Water (93 ml) was further added to the mixture, and the thus obtained mixture was then stirred for approximately 15 hours. Thereafter, the precipitated solid was collected by filtration and was then washed with a 27.5% acetonitrile aqueous solution (30 ml). The obtained solid was dried under reduced pressure to obtain the title compound (13.0 g, yield: 89%). The spectra of the resulting product, which were obtained using various devices, were matched with those obtained in Example 5.

Example 7

(1R,2R,4S)-2-{[(tert-Butoxycarbonyl)sulfamoyl] amino}-4-(dimethylcarbamoyl)cyclohexyl methanesulfonate tert-Butyl alcohol (117 ml) was mixed with acetonitrile (550 ml), and the mixed solution was then cooled to approximately 0° C. Thereafter, chlorosulfonyl isocyanate (101 ml) was added dropwise to the reaction solution over 3 hours. The obtained reaction solution was added dropwise to a mixed solution of acetonitrile (650 ml) and triethylamine (480 ml) over approximately 4 hours to prepare a solution of a Burgess-type reagent in acetonitrile.

An aqueous solution of (1S,3R,4R)-3-amino-4-hydroxy-N,N-dimethylcyclohexanecarboxamide (147.52 g) prepared by the same method as that in Reference Example 6 was cooled to approximately 5° C., and a 25% sodium hydroxide aqueous solution (184 ml) was then added to the reaction solution. This solution was added dropwise to the above described solution of the Burgess-type reagent in acetonitrile over approximately 30 minute, and water (100 ml) was then added thereto. The obtained mixture was stirred at approximately 5° C. for approximately 5 hours. Thereafter, the obtained reaction solution was concentrated to approximately 1400 ml, and ethyl acetate (1500 ml), citric acid (74.96 g) and water (100 ml) were then added thereto. The obtained mixture was heated to approximately 40° C., was then stirred, and was then left at rest. Thereafter, the organic layer was separated. The aqueous layer was extracted with ethyl acetate (1500 ml) again, and the organic layers were then gathered. The gathered organic layer was washed with 20% saline (760 ml), and was then concentrated to approximately 1000 ml. To the obtained concentrated solution, acetonitrile (1500 ml) was added, and the obtained mixture was then concentrated to approximately 600 ml. Thereafter, acetonitrile (1500 ml) was added to the concentrate, and the obtained mixture was further concentrated to obtain a solution of tert-butyl {[(1R,2R,5S)-5-(dimethylcarbamoyl)-2-hydroxycyclohexyl]sulfamoyl}carbamate in acetonitrile (approximately 600 ml). Acetonitrile (600 ml) was added to this acetonitrile solution (approximately 600 ml), and the obtained solution was then cooled to approximately 5° C. Methanesulfonyl chloride (77 ml) was added to the reaction solution, and N-methylmorpholine (136 ml) was then added dropwise to the mixed solution over approximately 15 minutes. The mixed solution was stirred for approximately 3 hours, and water (100 ml) and concentrated hydrochloric acid (49.39 g) were then added to the reaction solution. This reaction mixture was slowly added to water (2980 ml) that had been cooled to approximately 5° C., and the obtained mixture was then stirred for approximately 12 hours. Thereafter, the precipitated crystals were collected by filtration. The crystal cake was washed with a 27% acetonitrile aqueous solution (600 ml) and toluene (400 ml), and was then dried under reduced pressure to obtain the title compound (284.44 g).

Example 8

(1R,2R,4S)-2-{[(Benzyloxycarbonyl) sulfamoyl] amino}-4-(dimethylcarbamoyl)cyclohexyl methanesulfonate

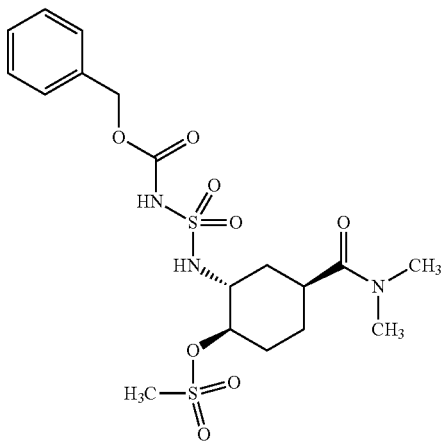 [SMILES: CN(C)C(=O)[C@H]1CC[C@@H](OS(C)(=O)=O)[C@H](NS(=O)(=O)NC(=O)OCc2ccccc2)C1]

Benzyl {[(1R,2R,5S)-5-(dimethylcarbamoyl)-2-hydroxycyclohexyl]sulfamoyl}carbamate (1.00 g) was added to methylene chloride (10 ml), and the obtained solution was then cooled to approximately 0° C. Triethylamine (0.52 ml) was added to the reaction solution, and methanesulfonyl chloride (0.28 ml) was then added dropwise to the mixed solution. The obtained mixture was stirred for approximately 1 hour. The precipitated crystals were collected by filtration, and were then washed with methylene chloride (1 ml). The obtained crystals were dried under reduced pressure to obtain 866 mg of the title compound (yield: 72%).

$^1$H-NMR (CDCl$_3$) δ: 1.51-1.66 (2H, m), 1.81-1.87 (1H, m), 1.96-2.01 (2H, m), 2.20-2.26 (1H, m), 2.76-2.88 (1H, m), 2.91 (3H, s), 2.99 (3H, s), 3.04 (3H, s), 4.05-4.10 (1H, m), 4.62-4.66 (1H, m), 5.15 (1H, d, J=14 Hz), 5.19 (1H, d, J=14 Hz), 5.65 (1H, br), 7.31-7.37 (6H, m).

Example 9

(1R,2R,4S)-2-{[(t-Butoxycarbonyl) sulfamoyl] amino}-4-(dimethylcarbamoyl)cyclohexyl 4-methylbenzenesulfonate

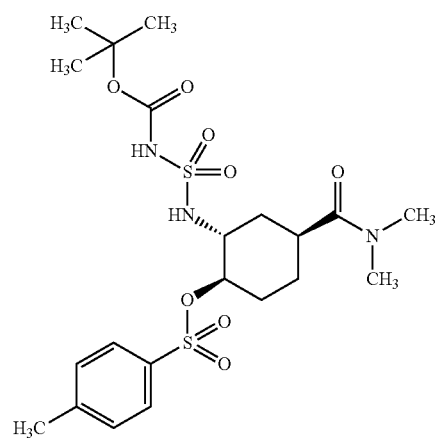

t-Butyl {[(1R,2R,5S)-5-(dimethylcarbamoyl)-2-hydroxycyclohexyl]sulfamoyl}carbamate (200 mg) was dissolved in dichloromethane (2.0 mL), and p-toluenesulfonyl chloride (136 mg) and N-methylimidazole (87.0 mL) were then added to the obtained solution. The obtained mixture was stirred at room temperature for approximately 20 hours. Thereafter, the reaction mixture was purified by silica gel column chromatography to obtain the title compound (107 mg, yield: 38%) in the form of powder.

$^1$H-NMR (CDCl3) δ: 1.47 (9H, s), 1.52-1.65 (2H, m), 1.70-1.78 (2H, m), 1.81-1.87 (1H, m), 2.18-2.27 (1H, m), 2.44 (3H, s), 2.77-2.83 (1H, m), 2.90 (3H, s), 3.02 (3H, s), 3.78-3.82 (1H, m), 4.64-4.66 (1H, m), 5.85-5.91 (1H, m), 7.34 (2H, d, J=7.9 Hz), 7.81 (2H, d, J=8.4 Hz)

Example 10 tert-Butyl(3aS,6S,7aR)-6-(dimethylcarbamoyl)-2,2-dioxohexahydro-2,1,3-benzothiadiazole-1(3H)-carboxylate

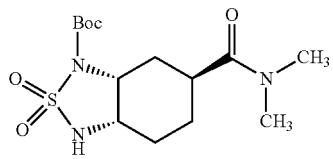 [SMILES: CN(C)C(=O)[C@H]1CC[C@@H]2NS(=O)(=O)N(C(=O)OC(C)(C)C)[C@@H]2C1]

Methylene chloride (200 ml) and triethylamine (18.5 ml) were added to tert-butyl {[(1R,2R,5S)-5-(dimethylcarbamoyl)-2-hydroxycyclohexyl]sulfamoyl}carbamate (20 g), and the obtained solution was then cooled to approximately 0° C. Methanesulfonyl chloride (5.2 ml) was added dropwise to the reaction solution, and the obtained mixture was then stirred for approximately 1 hour. Thereafter, water (100 ml) was added to the reaction mixture, and the organic layer was then separated. The solvent was distilled off from the organic layer under reduced pressure. To the residue, acetonitrile (200 ml) and triethylamine (15.4 ml) were added, and the obtained mixture was then heated to approximately 90° C., followed by stirring the mixture for approximately 2 hours. Thereafter, the reaction mixture was cooled to room temperature, 10% saline (100 ml) was then added to the mixture, and the organic layer was then separated. The aqueous layer was extracted with ethyl acetate (100 ml) again. The gathered organic layers were concentrated, and the obtained residue was purified by silica gel column chromatography to obtain the title compound (14.02 g, yield: 74%) in the form of powder.

$^1$H-NMR (CDCl$_3$) δ: 1.52 (9H, s), 1.66-1.79 (2H, m), 1.89-1.96 (1H, m), 2.10-2.21 (3H, m), 2.92 (3H, s), 2.92-2.98 (1H, m), 3.02 (3H, s), 3.86-3.90 (1H, m), 4.67-4.71 (1H, m), 4.81-4.83 (1H, br, NH).

HRMS (ESI$^-$): calculated for C$_{14}$H$_{25}$N$_3$O$_5$S, M–H$^-$ m/z 346.1437.
Found m/z 346.1446.

Example 11

Benzyl(3aS,6S,7aR)-6-(dimethylcarbamoyl)-2,2-dioxohexahydro-2,1,3-benzothiadiazole-1(3H)-carboxylate

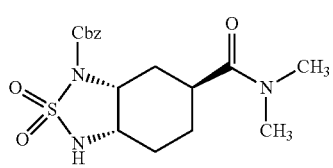 [SMILES: CN(C)C(=O)[C@H]1CC[C@@H]2NS(=O)(=O)N(C(=O)OCc3ccccc3)[C@@H]2C1]

Triethylamine (5 ml) was added to (1R,2R,4S)-2-{[(benzyloxycarbonyl)sulfamoyl]amino}-4-(dimethylcarbamoyl)cyclohexyl methanesulfonate (500 mg), and the obtained solution was then heated to approximately 90° C. The reaction solution was stirred for approximately 4 hours. Thereafter, the reaction mixture was cooled to room temperature, and the solvent was then concentrated and distilled off. The residue was added to methylene chloride (10 mL), a 1 mol/l hydrochloric acid solution (5 ml) was then added to separate the solution and the organic layer was then removed. The organic layer was concentrated under reduced pressure, and the residue was then purified by thin-layer chromatography to obtain 399 mg of the title compound (yield: 75%) in the form of an oily product.

$^1$H-NMR (CDCl$_3$) δ: 1.65-1.81 (2H, m), 1.89-1.97 (1H, m), 2.01-2.23 (3H, m), 2.90 (3H, s), 2.91-2.93 (1H, m), 2.94 (3H, s), 3.89-3.93 (1H, m), 4.80-4.85 (1H, m), 5.28 (1H, d, J=12.0 Hz), 5.33 (1H, d, J=12.0 Hz), 7.29-7.41 (5H, m).

Example 12

Benzyl(3aS,6S,7aR)-6-(dimethylcarbamoyl)-2,2-dioxohexahydro-2,1,3-benzothiadiazole-1(3H)-carboxylate Benzyl {[1R,2R,5S)-5-(dimethylcarbamoyl)-2-hydroxycyclohexyl]sulfamoyl}carbamate (1.00 g) was added to methylene chloride (10 ml), and triethylamine (1.76 ml) was then added to the obtained solution. Thereafter, methanesulfonyl chloride (0.28 ml) was added dropwise to the mixed solution, and the obtained mixture was then stirred for approximately 1 hour. Thereafter, triethylamine (2.00 ml) was added to the reaction mixture, and the obtained mixture was then heated to approximately 80° C., followed by stirring the mixture for approximately 4 hours. Thereafter, the reaction mixture was purified by thin-layer chromatography to obtain 545 mg of the title compound (yield: 57%) in the form of an oily product.

LC-MS (ESI): [M+H]$^+$=382, [M–H]$^-$=380 (retention time: 12.1 minutes)
HPLC conditions
Detection: 210 nm
Column: L-Column ODS (4.6 mm ID×250 mm, 5 μm)
Flow rate: 1.0 ml/min
Mobile phase: liquid A: 10 mM ammonium acetate aqueous solution, liquid B: MeCN
Gradient conditions (concentration of liquid B): 10%→80% (0-15 minutes), 80% (15-17 minutes), and 10% (17.01-23 minutes)

Example 13

Benzyl {[(1S,3S,6R)-3-(dimethylcarbamoyl)-7-azabicyclo[4.1.0]hepta-7-yl]sulfonyl}carbamate

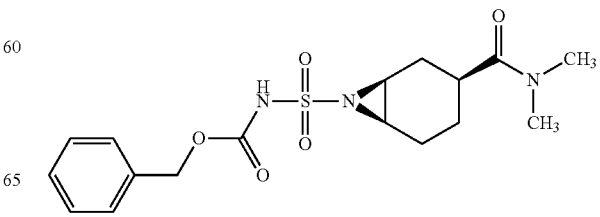

Under the above described reaction conditions in Example 12, after triethylamine had been added and the obtained mixture had been then stirred at approximately 80° C. for approximately 1 hour, the reaction was terminated, so as to obtain the title compound.

LC-MS (ESI): $[M+H]^+=382$, $[M-H]=380$ (retention time: 8.1 minutes)
(analyzed under the same HPLC conditions as those of Example 12)

Example 14 tert-Butyl(1R,2S,5S)-2-amino-5-[(dimethylamino)carbonyl]cyclohexylcarbamate oxalate (1)

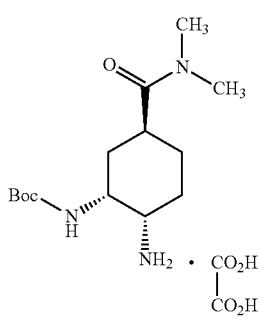

(1R,2R,4S)-2-{[(tert-butoxycarbonyl)sulfamoyl]amino}-4-(dimethylcarbamoyl)cyclohexyl methanesulfonate (100 g) and triethylamine (34.9 ml) were added to acetonitrile (250 ml), and the obtained mixture was then heated to approximately 60° C. Then, the reaction mixture was stirred for approximately 4 hours. Thereafter, an aqueous solution (150 ml) of 67% pyridine was added dropwise to the reaction solution, and the obtained mixture was then refluxed for approximately 4 hours. Thereafter, the reaction mixture was cooled to approximately 50° C., and 10% saline (200 ml), toluene (1000 ml) and a 48% sodium hydroxide aqueous solution (80 ml) were added to the mixture. The thus obtained mixture was stirred at approximately 50° C. for approximately 15 minutes, and the organic layer was then separated. 22% saline (500 ml) and a 48% sodium hydroxide aqueous solution (80 ml) were added to the aqueous layer again, the obtained mixture was then stirred at approximately 50° C. for approximately 15 minutes, and the organic layer was then separated. The organic layers were gathered, and the gathered organic layer was then concentrated to approximately 150 ml. Thereafter, acetonitrile (500 ml) was added to the concentrate, and the obtained mixture was further concentrated to approximately 100 ml. Acetonitrile (1000 ml) was added to the residue, and the precipitate was then filtered off. Water (50 ml) was added to the filtrate, and the obtained mixture was then heated to approximately 60° C. Thereafter, a solution of oxalic acid (20.3 g) in acetonitrile (300 ml) was added dropwise to the reaction mixture, and the thus obtained mixture was then stirred for approximately 1 hour. Thereafter, the reaction mixture was cooled to room temperature, and it was further stirred for approximately 1 hour. The precipitated crystals were collected by filtration, and the filtered crystals were then washed with a 7% aqueous acetonitrile solution (375 ml). A monohydrate of the obtained title compound was dried at approximately 60° C. under reduced pressure to convert it to an anhydride, so as to obtain the title compound (1) (69.5 g, yield: 82%).

Various spectrum data of the obtained compound (1) were matched with those described in International Publication No. WO 2007/032498.

Example 15 tert-Butyl(1R,2S,5S)-2-amino-5-[(dimethylamino)carbonyl]cyclohexylcarbamate oxalate (1)

Acetonitrile (360 ml) and triethylamine (26.6 ml) were added to (1R,2R,4S)-2-{[(tert-butoxycarbonyl)sulfamoyl]amino}-4-(dimethylcarbamoyl)cyclohexyl methanesulfonate (80 g), and the obtained solution was then heated to approximately 70° C. The reaction solution was stirred for approximately 2 hours to obtain a solution of tert-butyl(3aS,6S,7aR)-6-(dimethylcarbamoyl)-2,2-dioxohexahydro-2,1,3-benzothiadiazole-1(3H)-carboxylate in acetonitrile (467 ml).

Water (20 ml) and pyridine (80 ml) were added to the above described acetonitrile solution (467 ml), and the obtained solution was then heated to approximately 75° C. Then, the reaction solution was stirred for approximately 6 hours. Thereafter, the reaction solution was cooled to approximately 50° C., and water (80 ml), toluene (800 ml), 20% saline (80 ml) and a 25% sodium hydroxide solution (120 ml) were then added to the reaction solution. Thereafter, the mixed solution was left at rest, and the organic layer was then separated. The obtained organic layer was successively washed with 20% saline (80 ml) and a 25% sodium hydroxide solution (16 ml), and the obtained organic layer was then concentrated to approximately 240 ml. A procedure to add toluene (320 ml) to the concentrated solution and then to concentrate the mixed solution to approximately 240 ml was carried out twice, and acetonitrile (400 ml) was then added to the concentrated solution. Insoluble matters were filtered off to obtain a solution of tert-butyl(1R,2S,5S)-2-amino-5-[(dimethylamino)carbonyl]cyclohexylcarbamate in acetonitrile (solution amount: approximately 640 ml).

Oxalic acid (16.24 g) was added to acetonitrile (640 ml) and water (40 ml), and the obtained solution was then heated to approximately 35° C. To this solution, a solution of tert-butyl(1R,2S,5S)-2-amino-5-[(dimethylamino)carbonyl]cyclohexylcarbamate prepared by the above described method in acetonitrile (approximately 640 ml) was added dropwise, and the obtained mixture was then stirred at approximately 35° C. for approximately 1 hour. Thereafter, the reaction solution was cooled to approximately 25° C., and was then stirred for approximately 1 hour. The precipitated crystals were filtered, and were then washed with 7% aqueous acetonitrile (300 ml) to obtain a monohydrate of the title compound (tert-butyl(1R,2S,5S)-2-amino-5-[(dimethylamino)carbonyl]cyclohexylcarbamate oxalate monohydrate). To this monohydrate of the title compound, acetonitrile (560 ml) was added, and the obtained mixture was then heated to approximately 70° C. The reaction mixture was stirred at this temperature for approximately 5 hours, and was then concentrated to approximately 320 ml. Thereafter, acetonitrile (320 ml) was added to the concentrated solution, and the obtained mixture was then cooled to approximately 25° C. The precipitated crystals were filtered and were then washed with acetonitrile (80 ml), followed by drying under reduced pressure, to obtain an anhydride of the title compound (55.74 g, yield: 82%).

Example 16 tert-Butyl(1R,2S,5S)-2-amino-5-[(dimethylamino)carbonyl]cyclohexylcarbamate sulfate

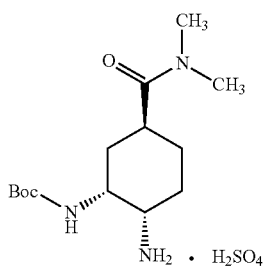

[(1R,2R,4S)-2-{[(tert-butoxycarbonyl)sulfamoyl]amino}-4-(dimethylcarbamoyl)cyclohexyl methanesulfonate (5.0 g) and triethylamine (1.66 ml) were added to acetonitrile (25 ml), and the obtained mixture was then heated to approximately 60° C. Then, the reaction solution was stirred for approximately 4 hours. Thereafter, a 67% pyridine aqueous solution (150 ml) was further added dropwise to the reaction solution, and the reaction mixture was then refluxed for approximately 4 hours. Thereafter, the reaction mixture was cooled to room temperature and was then stirred overnight. The precipitated crystals were collected by filtration, and the filtered crystals were then washed with acetonitrile (25 ml). The obtained crystals were dried under reduced pressure to obtain the title compound (3.62 g, yield: 84%).

Example 17

Potassium [(1S,2R,4S)-2-(tert-butoxycarbonylamino)-4-(dimethylcarbamoyl)cyclohexyl]sulfamate

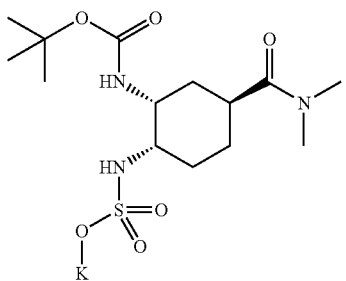

tert-Butyl(3aR,5S,7aS)-5-(dimethylcarbamoyl)-2,2-dioxo-3a,4,5,6,7,7a-hexahydro-1H-benzo[c][1,2,5]thiadiazole-3-carbamate (4.0 g), pyridine (4 ml), water (1 ml) and potassium carbonate (1.6 g) were added to acetonitrile (40 ml), and the obtained mixture was then stirred at approximately 70° C. After completion of the reaction, the reaction mixture was cooled to room temperature, the precipitated solid was then collected by filtration, and the obtained solid was then dried under reduced pressure. Methanol (53 ml) was added to the obtained solid (5.3 g), and the mixture was then stirred at room temperature. Thereafter, the precipitated solid was collected by filtration and was then washed with acetonitrile. The obtained solid was dried under reduced pressure to obtain the title compound (3.9 g, yield: 84%).

1H-NMR (DMSO-$d_6$) δ: 1.25-1.45 (3H, m), 1.39 (9H, s), 1.45-1.57 (1H, m), 1.78-1.82 (1H, m), 1.93-1.95 (1H, m), 2.71-2.80 (1H, m), 2.77 (3H, s), 2.94 (3H, s), 3.01-3.05 (1H, m), 3.78 (1H, br), 4.07 (1H, d, J=6.8 Hz), 6.42 (1H, br).

INDUSTRIAL APPLICABILITY

The production method of the present invention can be used as a method for industrially producing compound (X) and compound (X-a) that are FXa inhibitors.

The invention claimed is:

1. A method for producing a compound represented by the following formula (1d) or a salt thereof, or a hydrate thereof:

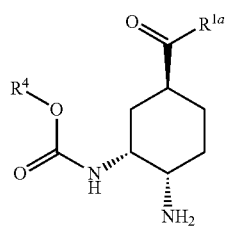

(1d)

wherein $R^{1a}$ represents a di(C1-C6 alkyl)amino group; and
$R^4$ represents a C1-C6 alkyl group or a benzyl group (wherein the benzyl group may have, on the benzene ring, one or two groups as substituents selected from the group consisting of a C1-C6 alkyl group, a C1-C6 alkoxy group, a nitro group, and a halogen atom),
the method comprising:
treating a compound represented by the following formula (4):

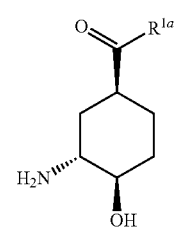

(4)

wherein $R^{1a}$ is as defined above,
with the following [solution A]:
[solution A] prepared by treating, in a solvent, a compound represented by the following formula (I):

$R^4$—OH  (I)

wherein $R^4$ is as defined above, with chlorosulfonyl isocyanate and a tertiary amine; or with the following [reagent B]:
[reagent B] that is a compound represented by the following formula (II):

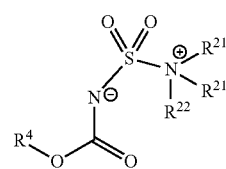

(II)

wherein $R^4$ represents a C1-C6 alkyl group or a benzyl group (wherein the benzyl group may have, on the benzene ring, one or two groups as substituents selected from the group consisting of a C1-C6 alkyl group, a C1-C6 alkoxy group, a nitro group, and a halogen atom); and $R^{21}$ and $R^{22}$ represent the following (a), (b) or (c):

(a) $R^{21}$ and $R^{22}$ are identical or different and each represent a C1-C6 alkyl group;

(b) $R^{22}$ represents a C1-C6 alkyl group, and the two $R^{21}$s, together with the nitrogen atom to which the $R^{21}$s bind, form a piperidine ring, a pyrrolidine ring or a 1,4-morpholine ring; or (c) the two $R^{21}$s and $R^{22}$, together with the nitrogen atom to which $R^{22}$ and the $R^{21}$s bind, form a 1,4-diazabicyclo[2.2.2]octane ring or a quinuclidine ring, so as to obtain a compound represented by the following formula (5):

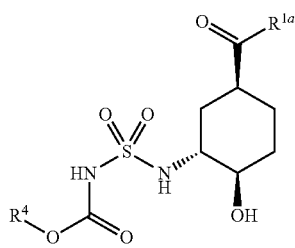

(5)

wherein $R^{1a}$ and $R^4$ are as defined above, treating, in the presence of a base, the compound represented by the formula (5) with a compound represented by the following formula (III):

$$R^6SO_2X \qquad (III)$$

wherein $R^6$ represents a C1-C6 alkyl group, a halo-C1-C6 alkyl group, or a phenyl group (wherein the phenyl group may have one or two groups as substituents selected from the group consisting of a C1-C6 alkyl group, a C1-C6 alkoxy group, a nitro group, and a halogen atom); and X represents a halogen atom, so as to obtain a compound represented by the following formula (6a):

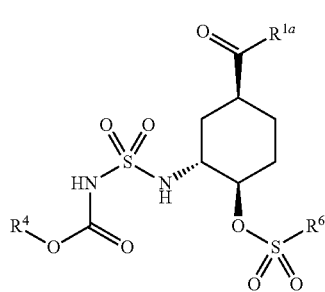

(6a)

wherein $R^{1a}$, $R^4$ and $R^6$ are as defined above, treating the compound represented by the formula (6a) with a base to obtain a compound represented by the following formula (8c):

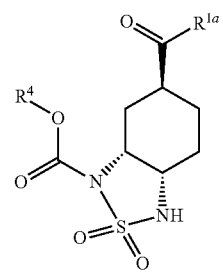

(8c)

wherein $R^{1a}$ and $R^4$ are as defined above, and
  performing desulfonylation of the compound represented by the formula (8c).

2. The production method according to claim 1, wherein the desulfonylation is carried out by treating the compound with water and a base.

3. The production method according to claim 2, wherein the base is a pyridine.

4. A method for producing a compound represented by the following formula (5):

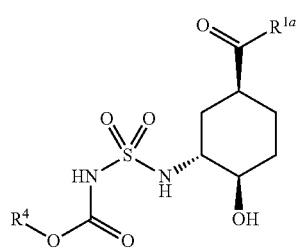

(5)

wherein $R^4$ represents a C1-C6 alkyl group or a benzyl group (wherein the benzyl group may have, on the benzene ring, one or two groups as substituents selected from the group consisting of a C1-C6 alkyl group, a C1-C6 alkoxy group, a nitro group, and a halogen atom); and $R^{1a}$ represents a di(C1-C6 alkyl)amino group, the method comprising treating a compound represented by the following formula (4):

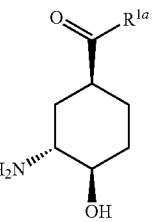

(4)

wherein $R^{1a}$ is as defined above, with the following [solution A]:

[solution A] prepared by treating, in a solvent, a compound represented by the following formula (I):

$$R^4\text{—OH} \qquad (I)$$

wherein $R^4$ is as defined above, with chlorosulfonyl isocyanate and a tertiary amine.

5. A method for producing a compound represented by the following formula (5):

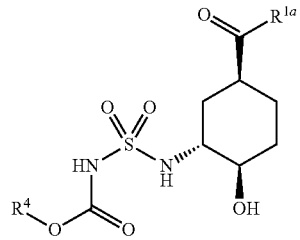

wherein $R^{1a}$ represents a di(C1-C6 alkyl)amino group; and
$R^4$ represents a C1-C6 alkyl group or a benzyl group (wherein the benzyl group may have, on the benzene ring, one or two groups as substituents selected from the group consisting of a C1-C6 alkyl group, a C1-C6 alkoxy group, a nitro group, and a halogen atom), the method comprising treating a compound represented by the following formula (4):

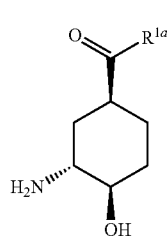

wherein $R^{1a}$ is as defined above, with the following [reagent B]:
[reagent B] that is a compound represented by the following formula (II):

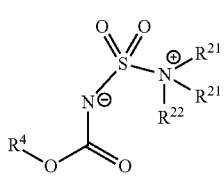

wherein $R^4$ is as defined above; and
$R^{21}$ and $R^{22}$ represent the following (a), (b) or (c):
(a) $R^{21}$ and $R^{22}$ are identical or different and each represent a C1-C6 alkyl group;
(b) $R^{22}$ represents a C1-C6 alkyl group, and the two $R^{21}$s, together with the nitrogen atom to which the $R^{21}$s bind, form a piperidine ring, a pyrrolidine ring or a 1,4-morpholine ring; or
(c) the two $R^{21}$s and $R^{22}$, together with the nitrogen atom to which $R^{22}$ and the $R^{21}$s bind, form a 1,4-diazabicyclo[2.2.2]octane ring or a quinuclidine ring.

6. The production method according to claim 1, wherein $R^{21}$ and $R^{22}$ each represent an ethyl group.

7. A method for producing a compound represented by the following formula (6a):

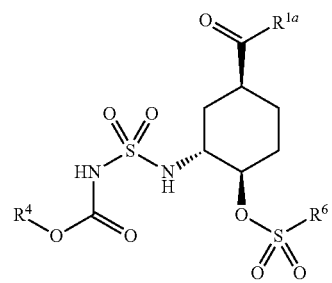

wherein $R^{1a}$ represents a di(C1-C6 alkyl)amino group;
$R^4$ represents a C1-C6 alkyl group or a benzyl group (wherein the benzyl group may have, on the benzene ring, one or two groups as substituents selected from the group consisting of a C1-C6 alkyl group, a C1-C6 alkoxy group, a nitro group, and a halogen atom); and
$R^6$ represents a C1-C6 alkyl group, a halo-C1-C6 alkyl group, or a phenyl group (wherein the phenyl group may have one or two groups as substituents selected from the group consisting of a C1-C6 alkyl group, a C1-C6 alkoxy group, a nitro group, and a halogen atom),
the method comprising treating, in the presence of a base, a compound represented by the following formula (5):

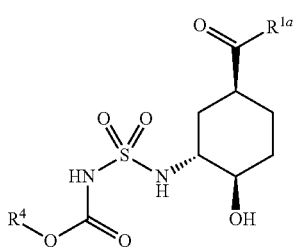

wherein $R^{1a}$ and $R^4$ are as defined above, with a compound represented by the following formula (III):

$$R^6SO_2X \qquad (III)$$

wherein $R^6$ is as defined above; and
X represents a halogen atom.

8. The production method according to claim 1, wherein $R^6$ represents a C1-C6 alkyl group.

9. The production method according to claim 1, wherein $R^6$ represents a methyl group.

10. A method for producing a compound represented by the following formula (8c):

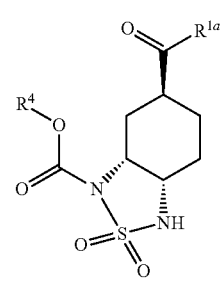

wherein $R^{1a}$ represents a di(C1-C6 alkyl)amino group; and

R⁴ represents a C1-C6 alkyl group or a benzyl group (wherein the benzyl group may have, on the benzene ring, one or two groups as substituents selected from the group consisting of a C1-C6 alkyl group, a C1-C6 alkoxy group, a nitro group, and a halogen atom), the method comprising treating a compound represented by the following formula (6a):

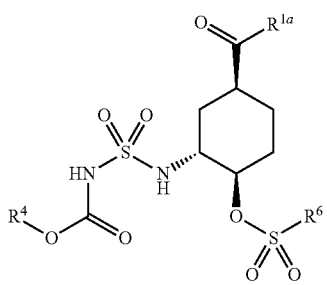

wherein $R^{1a}$ and $R^4$ are as defined above; and $R^6$ represents a C1-C6 alkyl group, a halo-C1-C6 alkyl group, or a phenyl group (wherein the phenyl group may have one or two groups as substituents selected from the group consisting of a C1-C6 alkyl group, a C1-C6 alkoxy group, a nitro group, and a halogen atom), with a base.

11. A method for producing a compound represented by the following formula (1d) or a salt thereof, or a hydrate thereof:

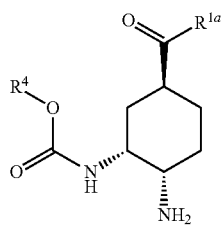

wherein $R^{1a}$ represents a di(C1-C6 alkyl)amino group; and

R⁴ represents a C1-C6 alkyl group or a benzyl group (wherein the benzyl group may have, on the benzene ring, one or two groups as substituents selected from the group consisting of a C1-C6 alkyl group, a C1-C6 alkoxy group, a nitro group, and a halogen atom), the method comprising desulfonylation of a compound represented by the following formula (8c):

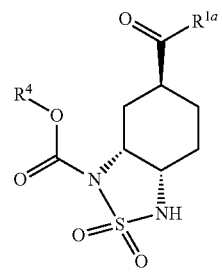

wherein $R^{1a}$ and $R^4$ are as defined above.

12. The production method according to claim 11, wherein the desulfonylation is carried out by treating the compound with water and a base.

13. The production method according to claim 12, wherein the base is a pyridine.

14. The production method according to claim 1, wherein $R^{1a}$ is a di(methyl)amino group.

15. The production method according to claim 1, wherein $R^4$ is a tert-butyl group or a benzyl group.

16. The production method according to claim 14, wherein the compound represented by the formula (1d) or a salt thereof, or a hydrate thereof is a sulfate of the compound represented by the formula (1d), an oxalate monohydrate of the compound represented by the formula (1d), or an oxalate of the compound represented by the formula (1d).

17. A method for producing a compound represented by the following formula (1b) or a salt thereof, or a hydrate thereof:

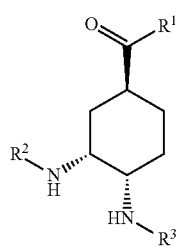

wherein $R^1$ represents a C1-C6 alkoxy group or a di(C1-C6 alkyl)amino group; and $R^2$ and $R^3$ each independently represent a hydrogen atom, a C1-C6 alkoxycarbonyl group, or a benzyloxycarbonyl group (wherein the benzyl group may have, on the benzene ring, one or two groups as substituents selected from the group consisting of a C1-C6 alkyl group, a C1-C6 alkoxy group, a nitro group, and a halogen atom), the method comprising desulfonylation of a compound represented by the following formula (8a):

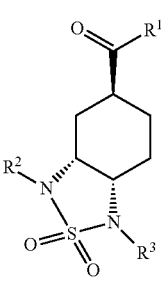

wherein $R^1$, $R^2$ and $R^3$ are as defined above.

18. A method for producing a compound represented by the following formula (1c) or a salt thereof, or a hydrate thereof:

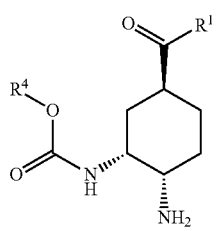

(1c)

wherein R¹ represents a C1-C6 alkoxy group or a di(C1-C6 alkyl)amino group; and

R⁴ represents a C1-C6 alkyl group or a benzyl group (wherein the benzyl group may have, on the benzene ring, one or two groups as substituents selected from the group consisting of a C1-C6 alkyl group, a C1-C6 alkoxy group, a nitro group, and a halogen atom), the method comprising desulfonylation of a compound represented by the following formula (8b):

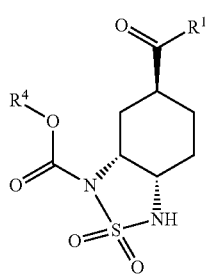

(8b)

wherein R¹ and R⁴ are as defined above.

19. A compound represented by the following formula (5):

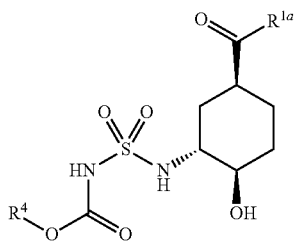

(5)

wherein R¹ᵃ represents a di(C1-C6 alkyl)amino group; and

R⁴ represents a C1-C6 alkyl group or a benzyl group (wherein the benzyl group may have, on the benzene ring, one or two groups as substituents selected from the group consisting of a C1-C6 alkyl group, a C1-C6 alkoxy group, a nitro group, and a halogen atom).

20. A compound represented by the following formula (6a):

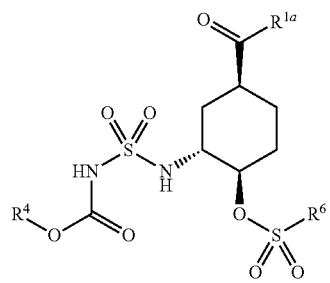

(6a)

wherein R¹ᵃ represents a di(C1-C6 alkyl)amino group;

R⁴ represents a C1-C6 alkyl group or a benzyl group (wherein the benzyl group may have, on the benzene ring, one or two groups as substituents selected from the group consisting of a C1-C6 alkyl group, a C1-C6 alkoxy group, a nitro group, and a halogen atom); and R⁶ represents a C1-C6 alkyl group, a halo-C1-C6 alkyl group, or a phenyl group (wherein the phenyl group may have one or two groups as substituents selected from the group consisting of a C1-C6 alkyl group, a C1-C6 alkoxy group, a nitro group, and a halogen atom).

21. The compound according to claim 20, wherein R⁶ represents a C1-C6 alkyl group.

22. The compound according to claim 20, wherein R⁶ represents a methyl group.

23. A compound represented by the following formula (8c):

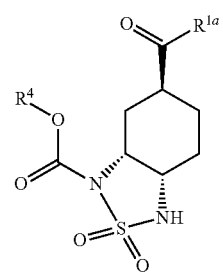

(8c)

wherein R¹ᵃ represents a di(C1-C6 alkyl)amino group; and

R⁴ represents a C1-C6 alkyl group or a benzyl group (wherein the benzyl group may have, on the benzene ring, one or two groups as substituents selected from the group consisting of a C1-C6 alkyl group, a C1-C6 alkoxy group, a nitro group, and a halogen atom).

24. The compound according to claim 19, wherein R¹ᵃ represents a di(methyl)amino group.

25. The compound according to claim 19, wherein R⁴ represents a tert-butyl group or a benzyl group.

26. A method for producing a compound represented by the following formula (X-a):

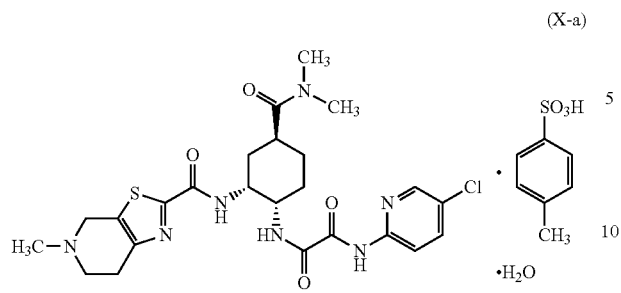

the method comprising: a step of treating a compound represented by the following formula (8d):

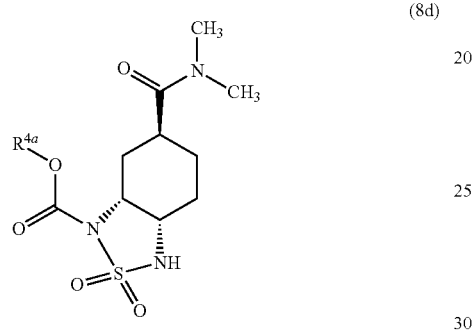

wherein $R^{4a}$ represents a C1-C6 alkyl group or a benzyl group (wherein the benzyl group may have, on the benzene ring, one or two groups as substituents selected from the group consisting of a C1-C6 alkyl group, a C1-C6 alkoxy group, a nitro group, and a halogen atom), with water and a base, to obtain a compound represented by the following formula (1f):

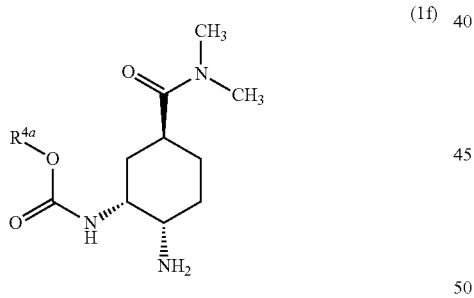

wherein $R^{4a}$ is as defined above,
treating, in the presence of a base, an oxalate or sulfate of the compound represented by the formula (1f) with a compound represented by the following formula (A-8):

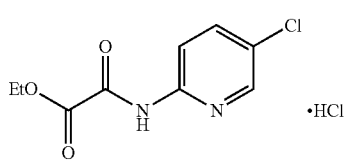

to obtain a compound represented by the following formula (A-9):

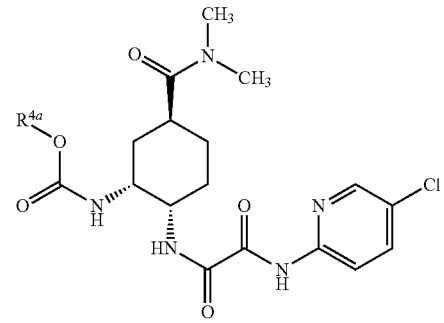

wherein $R^{4a}$ is as defined above,
deprotecting the compound represented by the formula (A-9) to obtain a compound represented by the following formula (A-10):

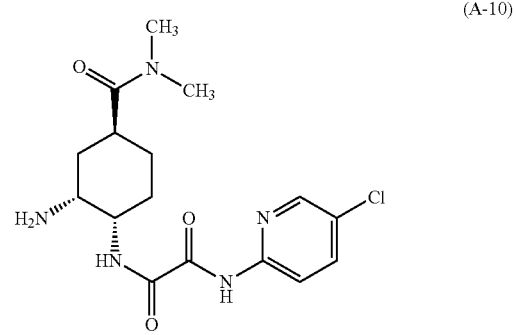 [SMILES: CN(C)C(=O)[C@H]1CC[C@H](NC(=O)C(=O)Nc2ccc(Cl)cn2)[C@H](N)C1]

and condensing the compound represented by the formula (A-10) or a salt thereof with a compound represented by the following formula (A-11):

to obtain a compound represented by the following formula (X):

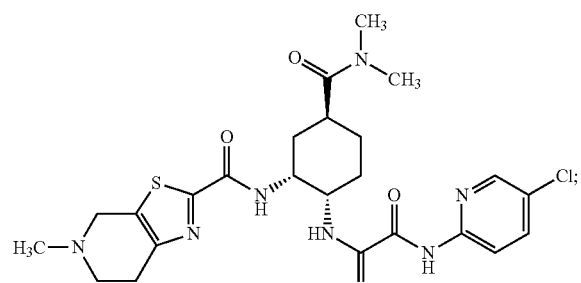

and
a step of treating the compound represented by the formula (X) with p-toluenesulfonic acid monohydrate in aqueous ethanol.

27. The production method according to claim 26, wherein $R^{4a}$ represents a tert-butyl group.

* * * * *